(12) United States Patent
Assaf et al.

(10) Patent No.: US 8,942,809 B2
(45) Date of Patent: *Jan. 27, 2015

(54) SYSTEMS AND METHODS FOR IMPROVING A COGNITIVE FUNCTION

(76) Inventors: Souhile Assaf, London (CA); Jessie Y. Shen, London (CA); Mandar Jog, London (CA)

( * ) Notice: Subject to any disclaimer, the term of this patent is extended or adjusted under 35 U.S.C. 154(b) by 503 days.

This patent is subject to a terminal disclaimer.

(21) Appl. No.: 12/885,223

(22) Filed: Sep. 17, 2010

(65) Prior Publication Data

US 2011/0009922 A1 Jan. 13, 2011

Related U.S. Application Data

(63) Continuation of application No. 11/824,077, filed on Jun. 28, 2007, now abandoned.

(60) Provisional application No. 60/806,053, filed on Jun. 28, 2006, provisional application No. 60/910,297, filed on Apr. 5, 2007, provisional application No. 60/910,391, filed on Apr. 5, 2007.

(51) Int. Cl.
*A61N 1/36* (2006.01)
*A61N 1/32* (2006.01)

(52) U.S. Cl.
CPC .............. *A61N 1/32* (2013.01); *A61N 1/36082* (2013.01)

USPC .......................................................... 607/45

(58) Field of Classification Search
USPC .......................................................... 607/45
See application file for complete search history.

(56) References Cited

U.S. PATENT DOCUMENTS

| | | | |
|---|---|---|---|
| 6,309,361 B1 * | 10/2001 | Thornton | 600/544 |
| 6,463,328 B1 * | 10/2002 | John | 607/45 |
| 6,539,263 B1 | 3/2003 | Schiff et al. | |
| 2002/0087201 A1 * | 7/2002 | Firlik et al. | 607/45 |
| 2005/0159790 A1 | 7/2005 | Shalev | |
| 2006/0020299 A1 | 1/2006 | Shalev | |
| 2006/0058853 A1 * | 3/2006 | Bentwich | 607/45 |
| 2006/0173510 A1 * | 8/2006 | Besio et al. | 607/45 |
| 2006/0212090 A1 * | 9/2006 | Lozano et al. | 607/45 |
| 2007/0265489 A1 * | 11/2007 | Fowler et al. | 600/12 |
| 2008/0046012 A1 * | 2/2008 | Covalin et al. | 607/2 |
| 2009/0248099 A1 * | 10/2009 | Assaf et al. | 607/3 |

* cited by examiner

*Primary Examiner* — Kennedy Schaetzle
(74) *Attorney, Agent, or Firm* — Eduardo Krupnik

(57) ABSTRACT

In many aspects, the invention relates to systems and methods for providing cognitive therapy through stimulation of activating and inhibiting neurons in the brain, thereby modulating neural firing rhythms. The stimulation of neurons is controlled through a feedback process whereby neuron firing rhythms are altered based on naturally occurring electrical and chemical activity in the brain. Neurons in specific regions of the brain may be targeted in order to establish neural signaling pathways and establish communication between these regions.

44 Claims, 13 Drawing Sheets

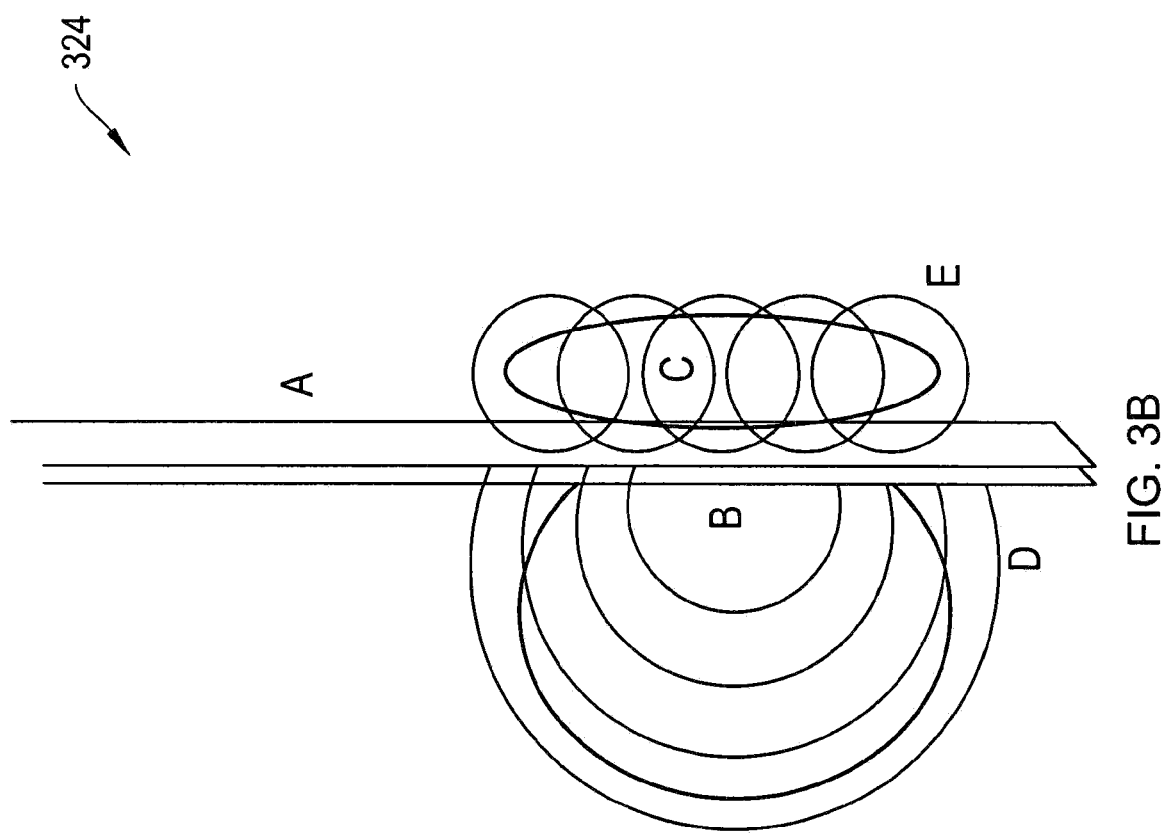

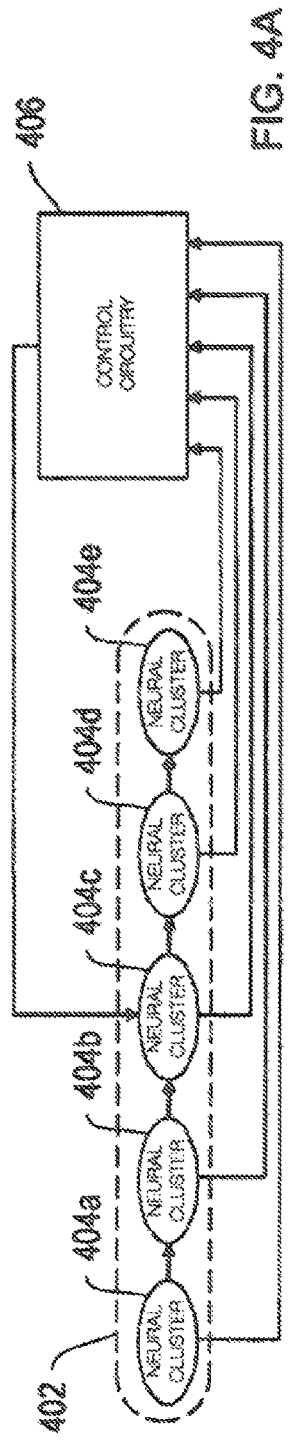
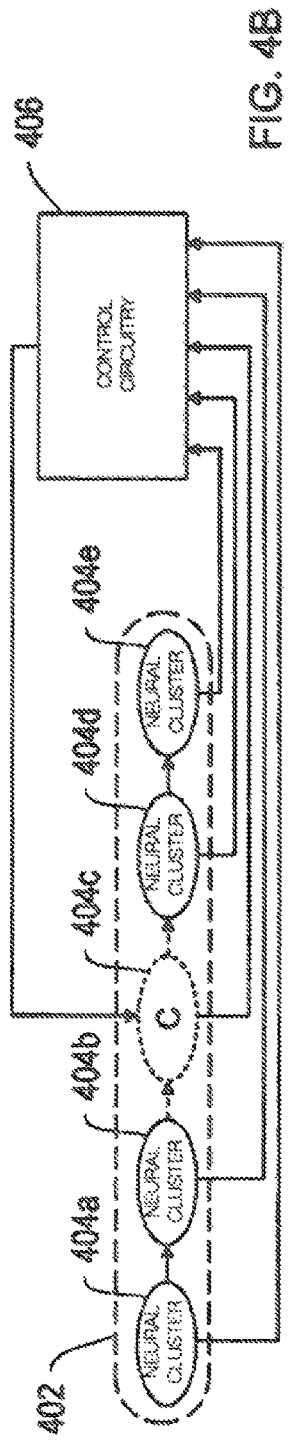
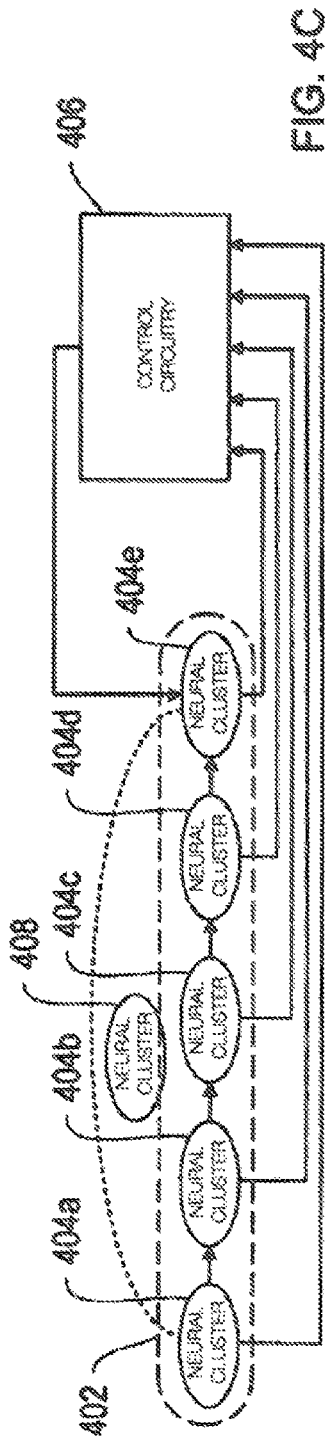

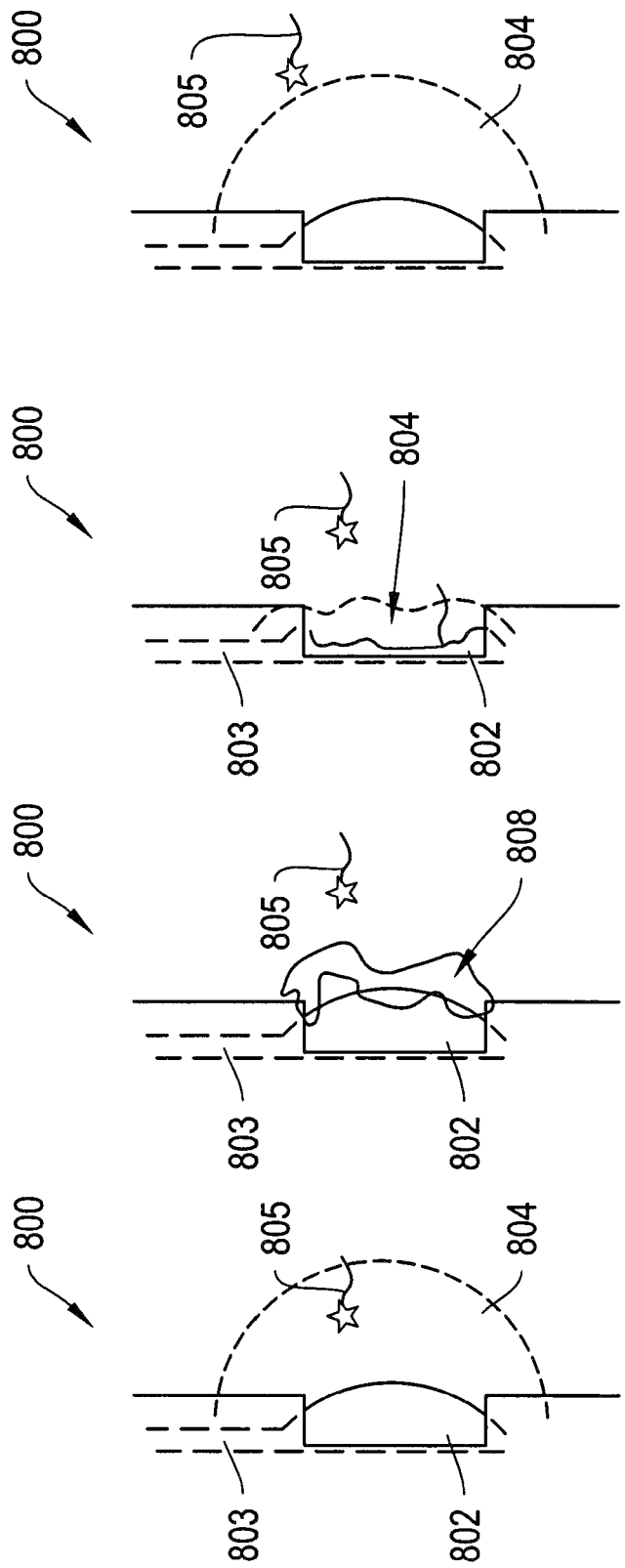

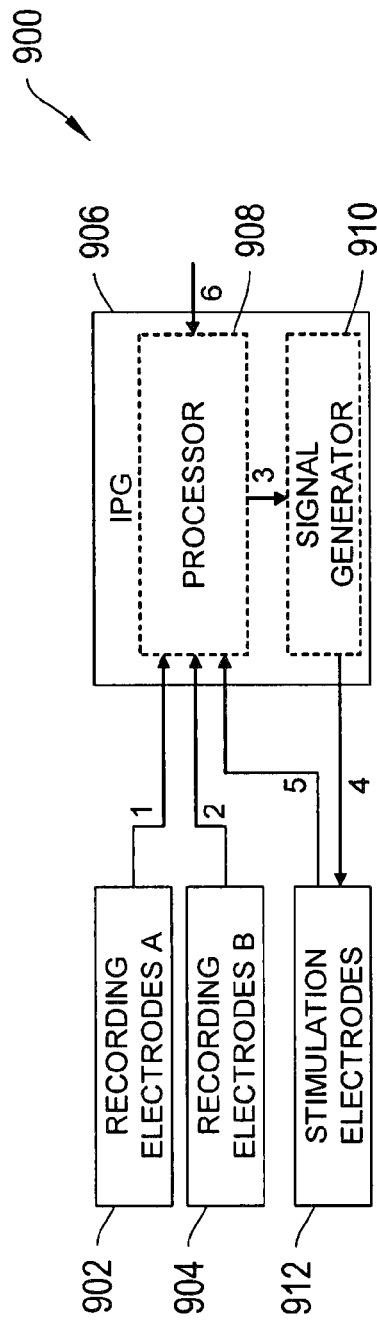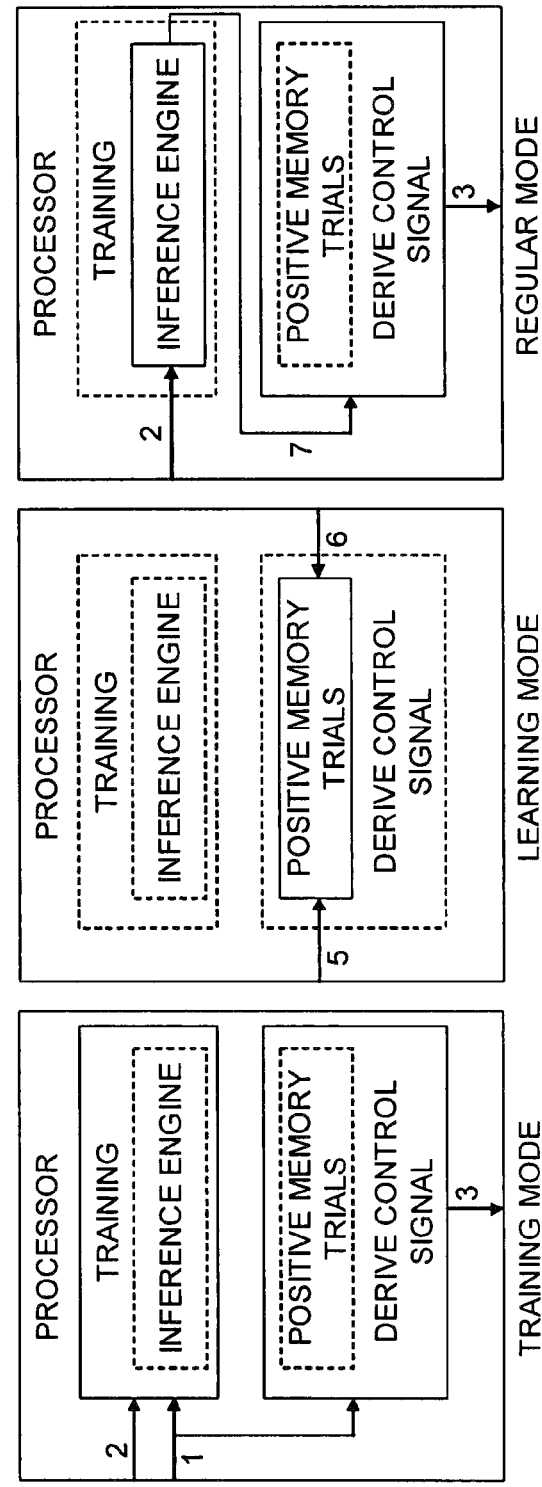

SYSTEMS AND METHODS FOR IMPROVING A COGNITIVE FUNCTION

CROSS-REFERENCE TO RELATED APPLICATION

This application is a continuation of U.S. application Ser. No. 11/824,077, filed Jun. 28, 2007, which claims priority to U.S. Provisional Patent Application No. 60/806,053, filed Jun. 28, 2006, U.S. Provisional Patent Application No. 60/910,297 filed Apr. 5, 2007, and U.S. Provisional Patent Application No. 60/910,391, filed Apr. 5, 2007, the entire contents of each of which are incorporated herein by reference.

FIELD OF INVENTION

The present invention relates to techniques for providing therapy to improve cognitive function such as learning and memory.

BACKGROUND OF THE INVENTION

Cognitive functions depend on different regions in the brain to process and communicate information with each other. The information is typically in the form of electrical and chemical signals that are communicated along neural signaling pathways between these regions. The neural signaling pathways are composed of electrically active brain cells called neurons. Many neurological disorders cause the degeneration of neurons in the brain and can therefore impair one or more cognitive functions.

Memory is a cognitive function that is facilitated in, among other places, the hippocampus and neocortex. During memory formation, information is transferred through neural signaling pathways both within and outside of the hippocampus. In some neurodegenerative diseases, including Alzheimer's disease, neurons in the hippocampus and neocortex degenerate, thereby disrupting communication along the neural signaling pathways.

There are currently no effective treatments for curing neurodegenerative disorders like Alzheimer's. Many researchers and scientists have proposed methods for implanting electrodes and catheters deep in the brain to stimulate desired regions including the hippocampus. However, these techniques simply provide jolts of electrical current to the brain that may even cause instability in those regions. They also suffer from a number of drawbacks including undesirable side effects, a short lifetime, unpredictability, and a lack of reproducibility.

Accordingly, there is a need for systems and methods for improving cognitive function through therapy.

SUMMARY OF THE INVENTION

The present invention is directed to systems and methods for improving cognitive function in the brain, especially in the event of the degeneration of neurons along neural signaling pathways. For purposes of clarity, and not by way of limitation, the systems and methods may be described herein in the context of improving particular cognitive functions that are associated with particular regions of the brain, such as memory with reference to the hippocampus and neocortex. However, it may be understood that the systems and methods of the present invention may be applied to improve any other cognitive function associated with any portion of the nervous system.

The systems and methods provide for intelligently controlling the neural firing rhythms in a region of the brain based on naturally occurring measures of cognitive activity such as neurophysiological markers (e.g., electrical and chemical activity) in that region or in a related region.

The system includes implantable elements and control circuitry for detecting electrical and chemical activity in the brain associated with a particular cognitive function and correlating the activity with a desired measure of a cognitive function. For example, electrical activity during a memory recall may be correlated with the nature of the memory recall (i.e., positive or negative recall). The nature of the memory recall, however, may also be measured with one or more neurophysiological markers (e.g., gamma rhythms). The electrical and/or chemical activity corresponding to a desired value of the neurological marker may be applied to a desired region of the brain to improve the cognitive function. As an example, hippocampal theta rhythm is necessary for memory formation, particularly for information processing. The theta rhythm includes extra-cellular currents that lie within a characteristic frequency range of about 4-8 Hz. The systems and methods provide for modulating the theta rhythm of the hippocampus by applying suitable electrical and chemical signals. These signals are controlled by continuously measuring other naturally occurring characteristics that the theta rhythms are associated with such as gamma oscillations in the hippocampus and neocortex. As another example, gamma (synchronicity) rhythm of the neocortex also plays a role in memory formation and other cognitive functions. The systems and methods also provide for recording and/or modulating the gamma rhythm of the neocortex by applying suitable electrical and chemical signals. Generally, the systems and methods provide for recording and/or modulating activity from one or more regions of the brain to improve one or more cognitive functions.

In one aspect the systems and methods described herein are methods for improving cognitive function in a patient. The method includes the steps of receiving a set of inputs from a first set of at least one region in a patient's brain, correlating the set of inputs with a set of neurophysiological markers of a cognitive function, and improving the cognitive function in the patient's brain by inducing a response in a second region of the brain, which response is selected based upon the correlations. In certain embodiments, the first region is the same as the second region.

In certain embodiments, the method further comprises determining an alertness level of the patient. The location of at least one of the first and second regions may be selected based on the alertness level. In certain embodiments, the response is selected based on the alertness level of the patient. In certain embodiments, the patient may exhibit two alertness levels that are determined based on whether the patient is awake or asleep. In such embodiments, the method comprises delivering at least two different responses that correspond to at least two alertness levels. The different responses may also be induced depending on the patient's alertness level. In certain embodiments, the alertness level is determined based on the set of inputs, such as theta rhythm.

In certain embodiments, the alertness level is high (e.g., this may indicate that the subject is awake and the therapy may be needed to promote information processing), and improving the cognitive function comprises inducing the neurons in the second region of the patient's brain to induce hippocampal theta rhythm. In certain embodiments, the alertness level is low (e.g., this may indicate that the subject is drowsy or asleep and the therapy may be needed to promote information consolidation), and improving the cognitive function comprises inducing the neurons in the second region of the patient's brain to induce hippocampal sharp waves. The alertness level may be determined based on a state of consciousness of the patient including awake and/or alert and/or sleep and/or unconsciousness. In certain embodiments, the alertness level is determined based whether the patient's brain is processing information or consolidating information or recalling information. In certain embodiments, the alertness level is user configurable, In certain embodiments, the alertness level is determined by a user.

In certain embodiments, the type of therapy or response is determined by the patient or care-giver. In one example, if the patient is going to sleep, the patient or the care-giver may set the therapy to a memory consolidation mode. During the day, the patient or the care-giver may set the therapy to information processing mode.

In certain embodiments, providing a inducing a response includes delivering an electrical signal and/or a chemical signal to neurons in the second region of the patient's brain to induce a desired neurophysiological response. In certain embodiments, the first and/or second regions include portions of the patient's brain that enable memory functions and are selected based on the alertness level.

In certain embodiments the systems and methods induce hippocampal theta rhythm by stimulating/activating neurons and/or inhibiting neurons in the second region. In certain embodiments, the neurons in the second region are located in the hippocampus and/or fornix and/or medial septum and/or supramammillary nucleus and/or posterior nucleus hypothalamus and/or nucleus pontis oralis and/or median raphe nucleus and/or neocortex and/or other portions of the brain and nervous system.

In certain embodiments, inducing a response includes delivering one or more electrical signals and/or one or more chemical signals to neurons in the second region of the patient's brain to induce activity (such as electrical and chemical signals) that may measure the performance of a memory process. The metric may include hippocampal sharp waves. In certain embodiments, the hippocampal sharp waves are induced by stimulating activating neurons and/or inhibiting neurons in the second region. In certain embodiments, the neurons in the second region are located CA1 and/or CA3.

In certain embodiments, hippocampal theta can be elicited by electrical stimulation of the supramammillary nucleus. The hippocampal theta may also be elicited by chemical stimulation with a carbachol injection. The hippocampal theta may also be reversibly inhibited by a procaine injection.

In certain embodiments, receiving a set of inputs includes measuring an electrical signal and/or a chemical signal. In certain embodiments, the electrical signal includes at least one of theta signal, a gamma signal, neocortical synchrony, delta activity, alpha activity recorded from the hippocampus and/or neocortex, and rhythmic discharges recorded from supramamillary nucleus and medial septum. The inputs may include any electrical, chemical, morphological and physical (e.g., blood flow) activity or signals in the brain. In certain embodiments, providing therapy includes delivering an electrical signal and/or a chemical signal to induce neurons in the second region of the patient's brain to generate a signal that is substantially similar to the at least one of the set of inputs.

In certain embodiments, neurophysiological markers are measures of a cognitive function. Neurophysiological markers may include electrical activity (e.g., neural firing patterns such as hippocampal theta activity and cortical theta activity) and chemical activity (e.g., neurotransmitters and other chemicals capable of mimicking neurotransmitters) in the brain. The neurophysiological markers may also include morphological and structural measurements of the different regions in the brain. The neurophysiological markers may further include other physical activities in the human body and the brain such as blood flow. As an example, functional MRI measurements may be used to track blood flow in the brain and are capable of identifying and measuring cognitive function based on the region receiving blood. In certain alternative embodiments, neurophysiological markers may also be linked to a behavioral trait or patient's speech and communication.

In certain embodiments, positive and negative memory recall events may include neurophysiological markers including at least one of hippocampal theta and cortical theta activity. In certain embodiments, correlating the set of inputs with a set of neurophysiological markers includes performing one or more cognitive exercises to associate one or more inputs with one or more neurophysiological markers. In such embodiments, during cognitive exercises, the implantable elements (such as electrodes) at recording sites and stimulation sites are recording the local activity. The recorded local activity at the recording sites may be associated with positive or negative recall events and to predict negative events. A database of positive events and the corresponding recorded activity may be built. In certain embodiments, when a negative event is predicted, activity recorded at the stimulation sites during positive events is superimposed on the local activity of the corresponding stimulation sites. In certain embodiment, the activity superimposed is an average of the events collected in the positive database.

In certain embodiments, the systems and methods further include steps of predicting negative memory events based on the inputs from the first set of at least one region. In such embodiments, the therapy may be applied by generating a signal that is substantially similar to the activity observed at the second set of at least one region during positive memory events. The systems and methods further include building a database of positive and negative memory events based on a set of cognitive exercises performed by the patient. The systems may include control circuitry configured to populate the databases and identify negative memory events based on referencing the inputs from the first region to the database of negative memory events and apply the corresponding activity from the database of positive memory event.

In certain embodiments, the system further builds an inference to differentiate the input conditions that each negative event triggers, such that the modulating pattern is determined based on successful trials with similar input conditions.

In certain embodiments, the systems and methods use recording sites that are not degenerating and stimulation sites that are continuing to fail. The system may be regularly trained by repeated cognitive exercises, such that the superimposed pattern may eventually replace the functions of the local neurons that have stopped functioning.

In certain embodiments, the neural signaling pathway include neurons connecting at least two of CA1, CA2, CA3, Dentate Gyrus, Entorhinal Cortex, Hilus, and subiculum. In certain embodiments, the neural signaling pathway includes the Perforant Path, Schaffer Collateral Pathway, and Associational Commissural Pathway. In certain embodiments, the neural signaling pathway includes posterior nucleus hypothalamus, supramammillary nucleus, medial septum, hippocampus, and neocortex.

In one aspect, a system for improving a cognitive function comprises a plurality of implantable elements for sensing and delivering signals within a brain, and control circuitry connected to the implantable elements. The control circuitry may be configured to receive a set of inputs from at least one of the plurality of implantable elements and correlate the set of inputs with a set of neurophysiological markers of a cognitive function. The control circuitry may be configured to determine a response based on the correlations, and induce the response in the brain using at least one of the plurality of implantable elements.

In certain embodiments, the implantable elements include electrodes capable of recording and generating electrical signals. In certain embodiments, the implantable elements include sensors capable of sensing chemical concentration. In certain embodiments, the implantable elements include catheters for delivering chemicals to the brain.

In certain embodiments, the implantable elements include at least one electrode recording information indicative of the memory activity, and at least one electrode that is suitable for long term implantation. In one embodiment, the electrode recording indicative activity is an electrode recording from single neuron or small cluster of neurons. Such an electrode may have a limited lifetime due to glial scarring or surface degradation of contact surfaces. The long term implantation electrode recording local field potential, intracortical EEG, or subdural EEG lasts longer due to a larger contact surface. In certain embodiments, an inference engine is capable of extracting single neuron activity from the long term electrodes.

In certain embodiments, the system includes a short term electrode and a long term electrode. In such embodiments, the control circuitry may be configured to determine if the short term electrode is function. In response to determining that the short term electrode is function, the control circuitry is configured to receive a first set of inputs from at least the short term electrode and a second set of inputs from at least the long term electrode. The control circuitry may also be configured to associate one or more of the first set of inputs with one or more of the second set of inputs. In certain embodiments, in response to determining that the short term electrode has failed, the control circuitry is configured to infer a first set of inputs based on the second set of inputs.

In one aspect, a method of improving a cognitive function in a patient comprises receiving a first signal from a first region of a neural signaling pathway of a patient's brain, determining a pacing signal that when applied to a second region of the brain induces the neurons in the second region of the brain to generate a second signal substantially similar to the first signal, and applying the pacing signal to the second region of the brain, thereby establishing a neural signaling pathway between the first and second regions and improving a cognitive function.

In certain embodiments, the method further comprises determining an alertness level of the patient. In certain embodiments, the method further comprises determining the therapy or response based on the alertness level. In certain embodiments, the patient exhibits at least two alertness levels. In certain embodiments, improving a cognitive function comprises improving at least two different cognitive functions that correspond to the at least two alertness levels.

In certain embodiments, the alertness level is determined based on the set of inputs. In certain embodiments, the alertness level is determined based on hippocampal theta rhythm. In certain embodiments, the alertness level is high and improving a cognitive function comprises inducing neurons in the second region of the patient's brain to induce hippocampal theta rhythm. In certain embodiments, the alertness level is low and improving a cognitive function includes inducing the neurons in the second region of the patient's brain to induce hippocampal sharp waves.

In certain embodiments, the alertness level is determined based on a state of consciousness of the patient including awake and/or alert and/or sleep and/or unconsciousness. In certain embodiments, the alertness level is determined based on whether the patient's brain is processing information or consolidating information. In certain embodiments, the alertness level is user configurable. In certain embodiments, the alertness level is determined by a user.

In certain embodiments, the first and/or second regions include portions of the patient's brain that enable memory functions and are selected based on the alertness level.

In certain embodiments, improving a cognitive function includes applying an electrical signal and/or a chemical signal to neurons in the second region of the patient's brain to induce a hippocampal theta rhythm. In certain embodiments, the theta rhythm is induced by stimulating activating neurons and/or inhibiting neurons in the second region. In certain embodiments, the neurons in the second region are located the nucleus pontis oralis and/or median raphe nucleus.

In certain embodiments, improving a cognitive function includes delivering at an electrical signal and/or a chemical signal to neurons in the second region of the patient's brain to induce hippocampal sharp waves. In certain embodiments, the hippocampal sharp waves are induced by stimulating activating neurons and/or inhibiting neurons in the second region.

In certain embodiments, receiving a first signal includes measuring an electrical signal and/or a chemical signal. In certain embodiments, the electrical signal includes a theta signal and/or a gamma signal. In certain embodiments, improving a cognitive function includes applying an electrical signal and/or chemical signal to induce neurons in the second region of the patient's brain to generate a signal that is substantially similar to the at least one of the set of inputs.

In certain embodiments, the cognitive function includes memory.

In certain embodiments, the neural signaling pathway include neurons connecting at least two of CA1, CA2, CA3, Dentate Gyrus, Entorhinal Cortex, Hilus, and subiculum.

In certain embodiments, the neural signaling pathway includes the Perforant Path, Schaffer Collateral Pathway, and Associational Commissural Pathway.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIGS. 3A and 3B depict a therapy system, according to illustrative embodiment of the invention.

FIGS. 4A-5 depict schemes for pacing one or more neural clusters in the brain according to an illustrative embodiment of the invention.

FIGS. 8A-8D depict the degradation of implantable elements in the brain.

FIGS. 9A-9D depict a therapy system, according to an illustrative embodiment of the invention.

DETAILED DESCRIPTION OF THE ILLUSTRATED EMBODIMENTS

Figure 1A:
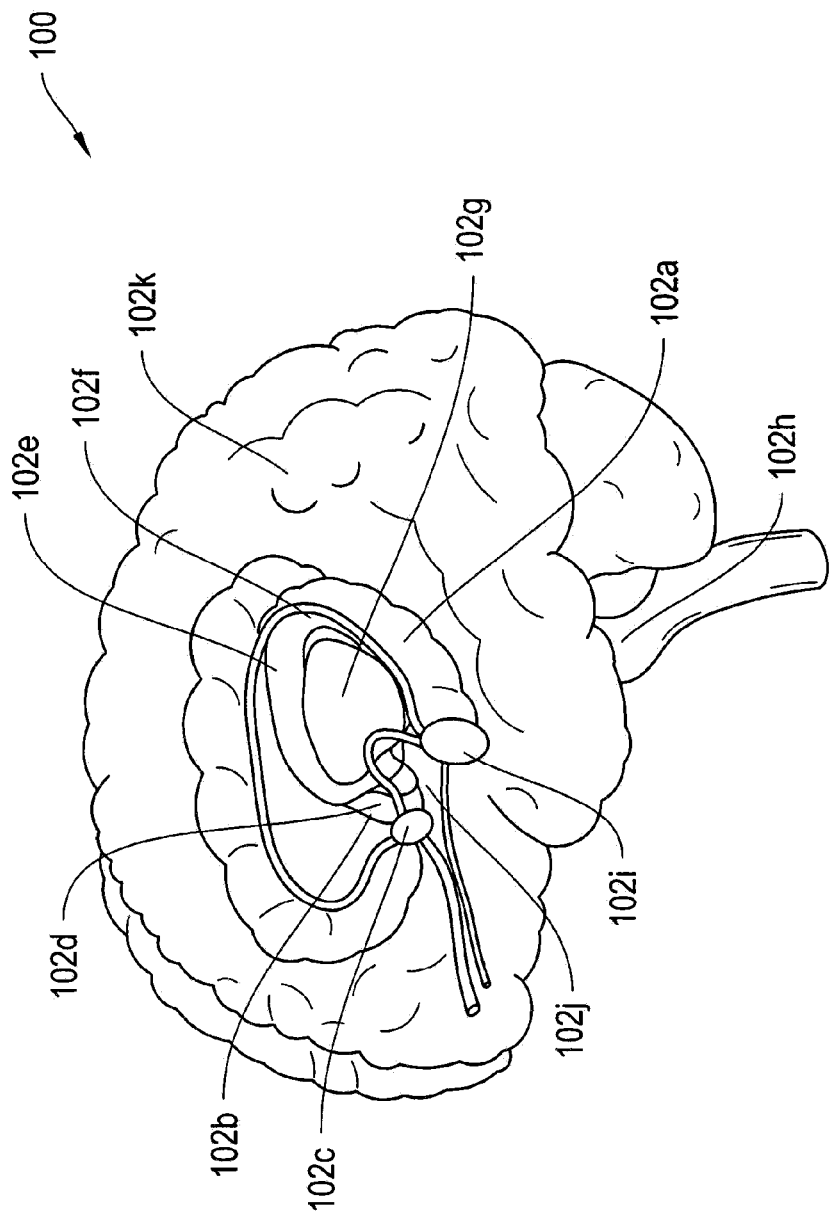
FIGS. 1A and 1B depict views of the brain and the hippocampus regions.

As will be seen from the following description, in some aspects, the invention relates to systems and methods for providing cognitive therapy through stimulation of activating and inhibiting neurons in the brain, thereby modulating neural firing rhythms.

The present invention may be embodied in various forms to analyze and treat disorders in cognitive function. Cognitive function includes attention, executive function, reaction time, learning information processing, conceptualization, problem solving, verbal fluency and memory (e.g., memory consolidation, short term memory, working memory, long term memory, declarative memory or procedural memory). Impairment in a cognitive function treated by the methods described herein can be an impairment in attention, which is the capacity or process of selecting out of the totality of available sensory or affective stimuli, those stimuli that are most appropriate or desirable for focus at a given time (Kinchla, R. A., et al., Annu. Rev. Psychol. 43:711-742 (1992)). A disorder in a cognitive process can result in an impairment in executive function, which are neuropsychological functions such as decision making, planning, initiative, assigning priority, sequencing, motor control, emotional regulation, inhibition, problem solving, planning, impulse control, establishing goals, monitoring results of action and self-correcting (Elliott, R., Br. Med. Bull. 65:49-59 (2003)). The cognitive impairment can be an impairment in alertness, wakefulness, arousal, vigilance, and reaction time information processing, conceptualization, problem solving and/or verbal fluency. Cognitive disorders include, for example without limitation, Alzheimer's disease, MCI (mild cognitive impairment), dementia, amnesia and memory disorders as can occur after injury, trauma, stroke, cranial irradiation, and in the context of genetic, congenital, infectious, autoimmune, toxic (drugs and alcohol), nutritional (vitamin deficiencies) metabolic, inflammatory, neurodegenerative neoplastic or idiopathic processes involving the brain. Some additional specific disorders where the therapy of the invention may be useful include: amnestic syndromes, Werkicke-Korsakoff and Korsakoff syndromes, Herpes encephalitis, severe hypoxia, vascular disorders, head injury, transient global amnesia, global amnesia epileptic amnesia, cerebral palsy, autism, mental retardation and attention deficit and hyperactivity disorders.

The application provides methods to improve cognitive function. The cognitive function can be assessed or determined by established techniques known to one skilled in the art. For example, memory can be assessed before, concomitantly with or after treatment of the individual by one or more well established tests known to one of skill in the art. Such tests include the Rey Auditory Verbal Learning Test (RAVLT); Cambridge Neuropsychological Test Automated Battery (CANTAB); a Children's Memory Scale (CMS); a Contextual Memory Test; a Continuous Recognition Memory Test (CMRT); a Denman Neuropsychology Memory Scale; a Fuld Object Memory Evaluation (FOME); a Graham-Kendall Memory for Designs Test; a Guild Memory Test; a Learning and Memory Battery (LAMB); a Memory Assessment Clinic Self-Rating Scale (MAC-S); a Memory Assessment Scales (MAS); a Randt Memory Test; a Recognition Memory Test (RMT); a Rivermead Behavioral Memory Test; a Russell's Version of the Wechsler Memory Scale (RWMS); a Test of Memory and Learning (TOMAL); a Vermont Memory Scale (VMS); a Wechsler Memory Scale; a Wide Range Assessment of Memory and Learning (WRAML); First-Last Name Association (Youngjohn J. R., et al., Archives of Clinical Neuropsychology 6:287-300 (1991)); Name-Face Association; Wechsler Memory Scale-Revised (Wechsler, D., Wechsler Memory Scale-Revised Manual, NY, N.Y., The Psychological Corp. (1987)); California Verbal Learning Test-Second Edition (Delis, D. C., et al., The Californian Verbal Learning Test, Second Edition, Adult Version, Manual, San Antonio, Tex.: The Psychological Corporation (2000)); Facial Recognition (delayed non-matching to sample); Cognitive Drug Research (CDR) Computerized Assessment Battery-Wesnes; Buschke's Selective Reminder Test (Buschke, H., et al., Neurology 24: 1019-1025 (1974)); Telephone Dialing Test; Brief Visuospatial Memory Test-Revised; and Test of Everyday Attention (Perry, R. J., et al., Neuropsychologia 38: 252-271 (2000)).

An improvement in cognitive function may be determined by an improvement in performance in a cognitive test, as described above. Alternatively, an improvement in cognitive function may also be established in a patient as a decrease in the decline of cognitive function, for example in a disorder characterized by a continuing decrease in cognitive function, e.g., Alzheimer's disease.

The patient receiving this treatment is any animal in need, including primates, in particular humans, and other mammals such as equines, cattle, swine and sheep; and poultry and pets in general.

The stimulation of neurons is controlled through a feedback process whereby neuron firing rhythms are altered based on naturally occurring electrical and chemical activity in the brain. Neurons in specific regions of the brain may be targeted in order to establish neural signaling pathways and establish communication between these regions.

To provide an overall understanding of the invention, certain illustrative embodiments will now be described, including the cognitive therapy scheme and constituent components thereof. However, it will be understood by one of ordinary skill in the art that the methods and systems described herein may be adapted and modified as is appropriate for the application being addressed and that the systems and methods described herein may be employed in other suitable applications, and that such other additions and modifications will not depart from the scope hereof.

Figure 1B:
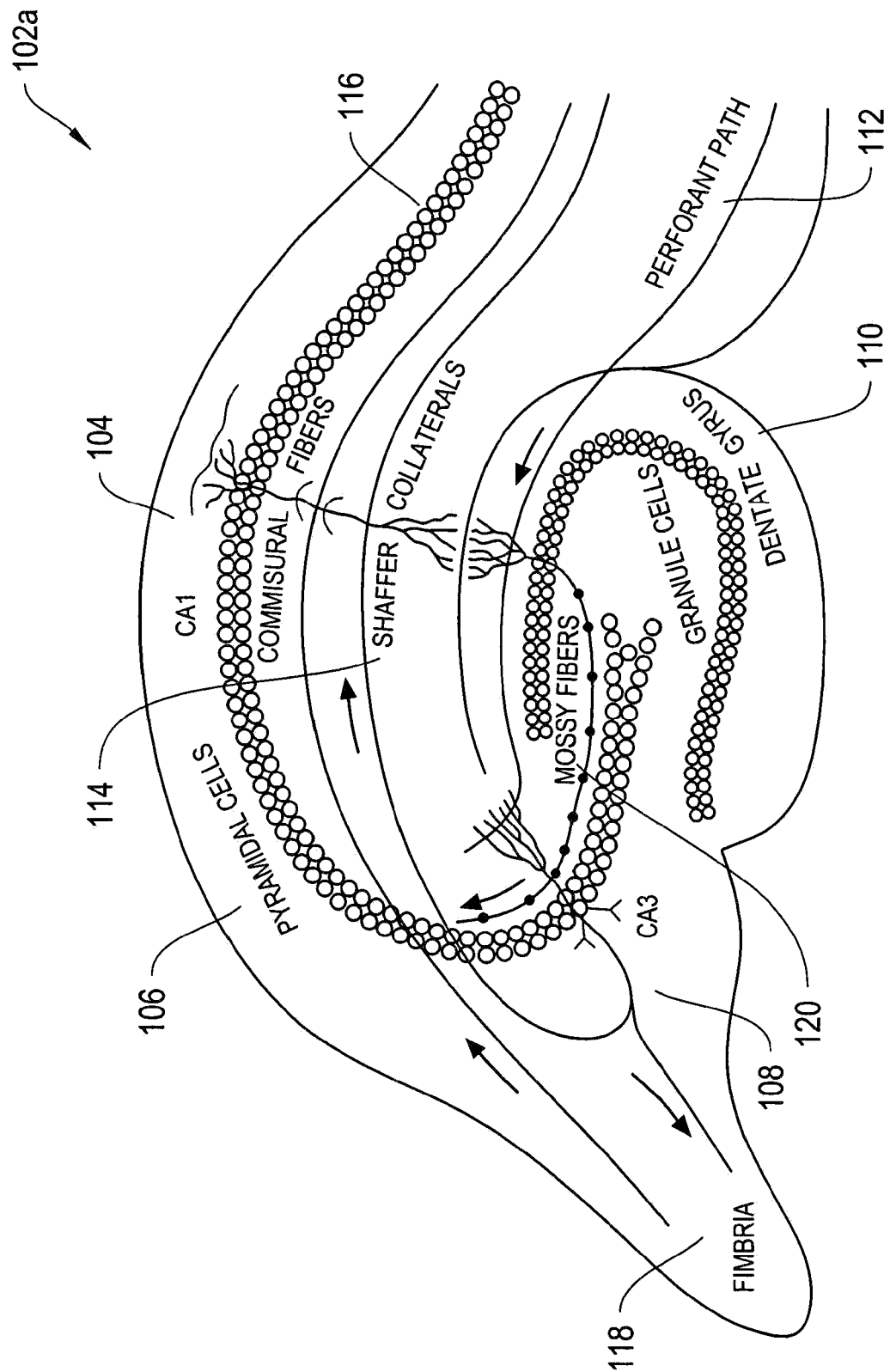

FIG. 1 shows a human brain 100 in which the hippocampus is a part of the brain that is located in the medial temporal lobe. The hippocampus forms part of the limbic system. Typical human brains have two hippocampi 102a and 102b, one in each side of the brain. The role of the hippocampus is in the formation of new memories about episodic events. The hippocampus is generally part of a larger medial temporal lobe memory system that is also responsible for general declarative memory (memories that be verbalized such as memory for facts). The hippocampus is also responsible for storing and processing spatial information. Studies in rats have shown that neurons in the hippocampus have spatial firing fields. As a result, the hippocampus is required for simple spatial memory tasks (e.g., finding the way back to a hidden goal). The hippocampus is also shown to modulate emotional reactions. Certain experiments have shown that mild stimulation of the hippocampus have an alerting reaction characterized with cortical de-synchronization, respiratory acceleration, and heart rate increase.

Around the hippocampus, there is septal nucleus (102c) and medial septum (102d). Medial septum is typically recognized as the pacemaker of the hippocampus. Furthermore, the hippocampus curls around the fornix (102e) and fimbria (102f), the thalamus (102g), raphe nuclei (102h), Amygdala (102i), supramammillary nucleus (102j), and neocortex (102k).

FIG. 2 depicts the anatomy of the hippocampus 102 and information flow through the various regions in the hippocampus. The hippocampal region generally refers to the dentate gyrus 110, the Cornu Ammonis fields CA1 104, CA2 106, CA3 108 (and CA4, frequently called the hilus and considered part of the dentate gyrus 110), and the subiculum.

Information flow through the hippocampus 102 proceeds from one region to another along neural signaling pathways. In particular, information flow proceeds from the dentate gyrus 110 to CA3 108 to CA1 104 to the subiculum, with additional input information at each stage and outputs at each of the two final stages. CA2 104 typically represents a small portion of the hippocampus 102 and, in general, is resistant to conditions that usually cause large amounts of cellular damage, such as epilepsy.

The perforant path 112, which brings information primarily from entorhinal cortex (but also perirhinal cortex, among others), is generally considered a main source of input to the hippocampus 102. Layer II of the entorhinal cortex (EC) brings input to the dentate gyrus and field CA3, while EC layer III brings input to field CA1 and the subiculum. The main output pathways of the hippocampus are the cingulum bundle and the fimbria/fornix, which arise from field CA1 104 and the subiculum.

Perforant path 112 input from EC layer II enters the dentate gyrus 110 and is relayed to region CA3 108 (and to mossy cells 120, located in the hilus of the dentate gyrus 110, which then send information to distant portions of the dentate gyrus 110 where the cycle is repeated). Region CA3 108 combines this input with signals from EC layer II and sends extensive connections within the region and also sends connections to region CA1 104 through a set of fibers called the Schaffer collaterals 114. Region CA1 104 receives input from the CA3 108 subfield, EC layer III and the nucleus reuniens of the thalamus (which project only to the terminal apical dendritic tufts in the stratum lacunosum-moleculare). In turn, CA1 104 projects to the subiculum as well as sending information along the aforementioned output paths of the hippocampus 102. The subiculum is typically the final stage in the pathway, combining information from the CA1 104 projection and EC layer III to also send information along the output pathways of the hippocampus.

The hippocampus also receives a number of subcortical inputs. In Macaca fascicularis 120, these inputs include at least one of the amygdala (specifically the anterior amygdaloid area, the basolateral nucleus, and the periamygdaloid cortex), the medial septum and the diagonal band of Broca, the claustrum, the substantia innominata and the basal nucleus of Meynert, the thalamus (including the anterior nuclear complex, the laterodorsal nucleus, the paraventricular and parataenial nuclei, the nucleus reuniens, and the nucleus centralis medialis), the lateral preoptic and lateral hypothalamic areas, the supramammillary and retromammillary regions, the ventral tegmental area, the tegmental reticular fields, the raphe nuclei (the nucleus centralis superior and the dorsal raphe nucleus), the nucleus reticularis tegementi pontis, the central gray, the dorsal tegmental nucleus, and the locus coeruleus.

Memory formation generally has two steps including information processing and information consolidation. During information processing, the information is temporarily stored in the CA3 108. During information consolidation, the information from the CA3 108 is transferred to the CA1 104 and subsequently onto the cortex.

The various regions in the brain (including the hippocampus) are composed of electrically active and electrically excitable cells called neurons. Neurons transfer information along the neural signaling pathway through synaptic transmission, whereby neurons communicate via chemical and electrical signals (e.g., action potentials) that are transferred from one neuron to another. Typically each neuron follows a firing pattern whereby the neuron generates an electrical or chemical signal in a train of spikes (e.g., action potentials) at regular intervals. A group of neurons in close proximity to each other may fire independently but still demonstrate an overall rhythm. This overall rhythm may exhibit certain patterns that may be associated with certain behavior.

As an example, the overall rhythm of hippocampal neurons may exhibit a theta rhythm having a frequency from about 4 Hz to about 8 Hz. The theta rhythm has been demonstrated as being an important requirement during the information processing stage of memory formation and may be manifested during some short term memory tasks. Theta rhythm is associated with gamma oscillations having a frequency of about 40 Hz to about 100 Hz recorded in the hilus and/or the CA1 104. Theta rhythm is also associated with sodium spike activities.

As another example, the overall rhythm of hippocampal neurons may exhibit sharp waves having a duration of about 40 to about 120 msec and a frequency of about 200 Hz. These sharp waves can be recorded in CA1 and/or CA3.

Damage to the hippocampus usually results in profound difficulties in forming new memories as well as affecting memories prior to damage. Disorientation and memory recall problems therefore appear as early symptoms in disorders affecting the hippocampus, such as Alzheimer's disease.

Electrical and/or chemical stimulation of regions or neural clusters in the hippocampus provides a therapy for improving memory formation. In particular, electrical and/or chemical stimulation of the hippocampal neurons can affect their firing patterns. For example, electrical stimulation has been demonstrated to disrupt theta activity, which in turn affects memory. Superimposing an artificial stimulating rhythm to the hippocampus improves memory performance in animals whose memory was partially impaired.

Alternatively, chemical stimulation may be provided as therapy for improving cognitive function. Any number of drugs may be administered as a chemical stimulation including, but not limited to, an anesthetic, a GABA agonist, a GABA antagonist, a glutamate antagonist, a glutamate agonist, a degrading enzyme, a reputake blocker, and a dopamine antagonist. An activating chemical may be used and includes any chemical that causes an increase in the discharge rate of the projection nerve cells from a region. An example (for projection neurons which receive glutamatergic excitation and GABA inhibition) would be an agonist of the transmitter substance glutamate (facilitating the excitation) or a GABA antagonist (blocking the inhibition). Conversely, a blocking chemical may be used and includes any chemical that inhibits the projection neurons thereby causing a decrease in the discharge rate of the projection nerve cells from a region. An example would be a glutamate antagonist (blocks excitatory input to the projection nerve cells) or a GABA agonist (enhances inhibition of the projection neurons).

Figure 2A:
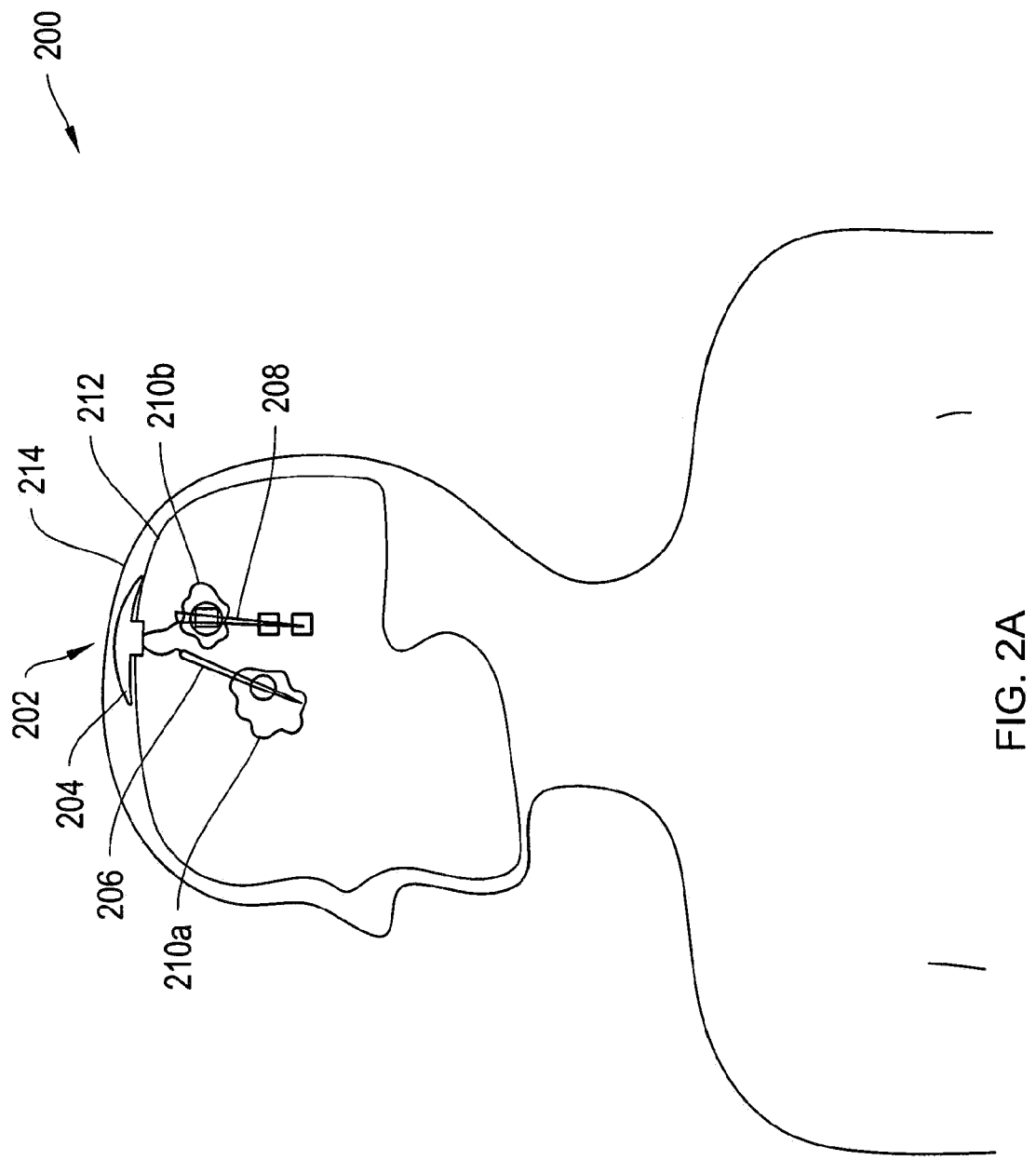
FIGS. 2A and 2B depict a therapy system, according to an illustrative embodiment of the invention.
Figure 2B:
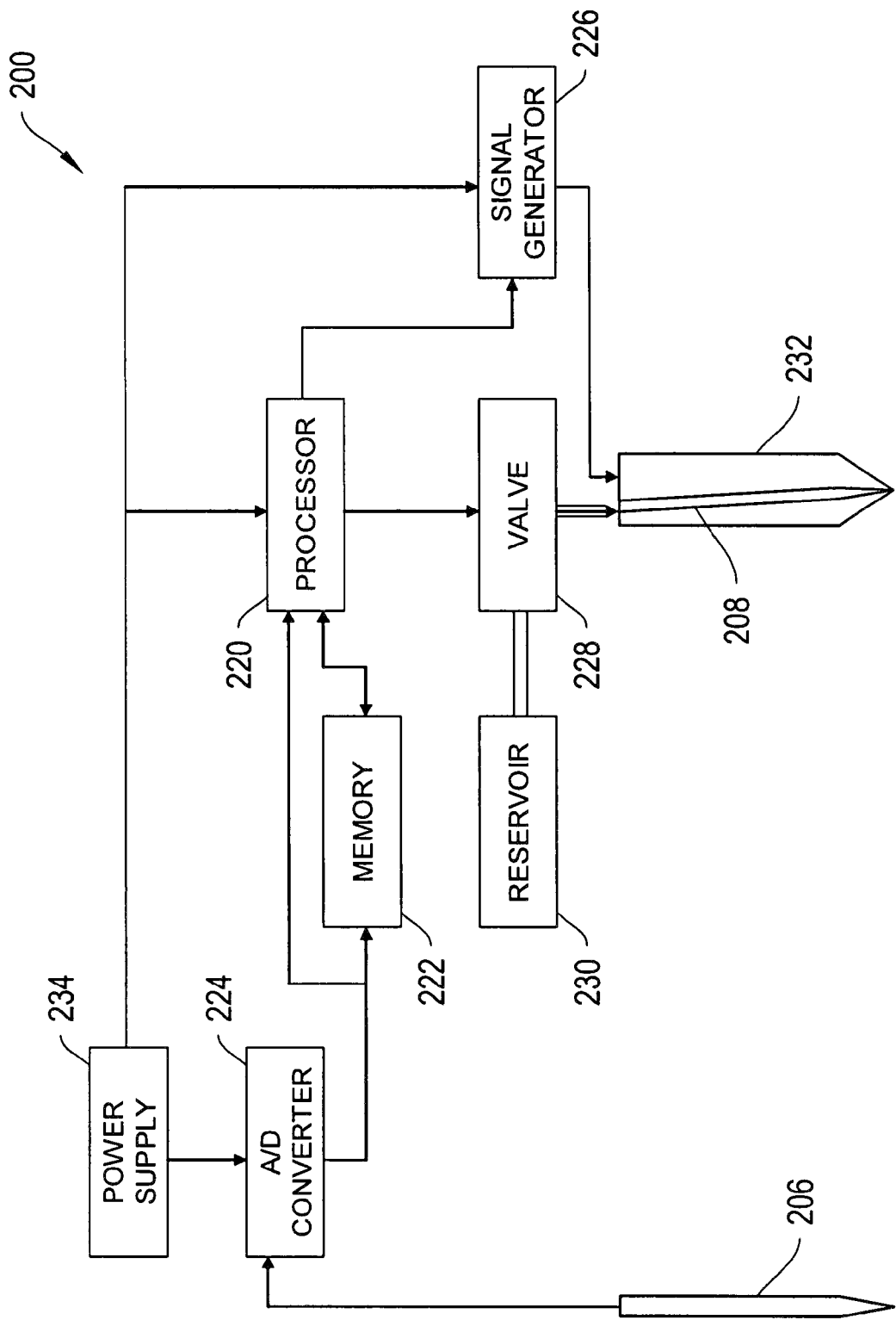

FIGS. 2A and 2B depict a therapy system 200 according to an illustrative embodiment of the invention. In particular, the therapy system 202 includes a pair of implantable elements 206 and 208 and control circuitry 204 located inside a casing 202. The casing placed on the skull 212 and underneath the scalp 214. A hole through the top portion of the skull allows the implantable elements 206 and 208 to be inserted into one or more regions of the brain. The casing 202 may be placed by rolling back the scalp, drilling a hole in the skull, cutting open the dura and other membranes, and using stereotactic frame or intraoperative MRI. The implantable elements 206 and 208 may be linked to the casing 202 by flexible interconnects. The interconnects are carefully lowered into the skull and the csing 202 is inserted in the drilled hole. Each of the implantable elements 206 and 208 are inserted in regions 210a and 210b of the brain. During operation, the implantable elements 206 and 208 record and/or stimulate neurons in these regions.

The implantable elements 206 and 208 may include electrodes to measure and record electrical signals. The electrodes may also be capable of generating electrical fields and thereby delivering electrical signals to a particular region of the brain. The implantable elements are generally narrow and include a pointed tip for penetrating through the brain. In certain embodiments, the electrodes include conductive channels to generate an electric field in the vicinity of the electrode. These conductive channels may be arranged in any suitable pattern along the electrode. The implantable elements 206 and 208 may also include chemical sensors to measure and record chemical concentrations, e.g., calcium and/or acetylcholine and/or neurotransmitters. The implantable elements 206 and 208 may include catheters and valves to deliver and control the release of chemical compounds into the brain. In certain embodiments, the implantable elements 206 and 208 may include electrical and chemical sensors and stimulators along with other components including light sources and electronic circuitry. One suitable type of implantable device is shown in U.S. Pat. No. 7,010,356, "Multichannel Electrode and Methods of Using Same," the entire contents of which is herein incorporated by reference. The implantable elements and circuitry may include MEMS based devices and nanostructures to allow for specific placement.

The casing may include a transcranial casing having suitable properties for implantation on the surface of the skull underneath the scalp.

In certain embodiments, the control circuitry includes electronic components for receiving, processing and generating signals to stimulate neural clusters. FIG. 2B is a block diagram depicting a therapy system 200 having control circuitry including a processor 220, memory/storage 222, an analog-to-digital converter 224, and a signal generator 226. The control circuitry is connected to a valve 228 that controls the flow of chemical compounds from a reservoir 230 to the implantable element 208. The various components in the system 200 are powered by power supply 234.

The processor 220 may include a single microprocessor or a plurality of microprocessors for configuring control circuitry as a multi-processor system. The memory 222 may include a main memory and a read only memory. The memory 222 may also include the mass storage device such as flash drives. The main memory 222 also includes dynamic random access memory (DRAM) and high-speed cache memory. In operation, the main memory 222 stores at least portions of instructions and data for execution by the processor 220.

In certain embodiments, the implantable devices 206 include sensors capable of detecting electrical activity and/or chemical concentrations in the brain and outputting an analog electrical signal that is representative of the activity or concentration. The system 200 includes an analog-to-digital converter 224 for receiving the measured analog signals from the implantable elements 206 and converting these signals to digital form for the processor 220.

The system 200 includes a signal generator 226 having circuitry that is capable of generating an electrical pacing signal based on a digital command from the processor 220. The pacing signal is sent to the implantable element 208 which delivers the signal to the brain.

The implantable element 208 may further include a catheter 232 for delivering chemical compounds to regions of the brain. These catheters may be connected to a chemical compound reservoir 230 via a programmable valve 228. The processor 220 may send control signals to open or close the valve 228 and thereby control the flow of the chemical compounds from the reservoir 230 to the brain via catheter 232.

Regions 210a and 210b may be part of the hippocampus and a cognitive function such as memory recall may be facilitated by neural communication between regions 210a and 210b. In certain embodiments, the regions 210a and/or 210b may include the medial septum, basalis nucleus, supramammillary nucleus, posterior nucleus hypothalamus, raphe nucleus, fornix, fimbria and neocortex. In particular, information may flow from region 210a to 210b. However, the neural signaling pathway between regions 210a and 210b may be damaged (e.g., due to degeneration of one or more neurons), causing diminished cognitive function. Cognitive functions such as memory recall are correlated with theta activity. The implantable element 206 may be used to record theta activity in region 210a. The control circuitry 216 may then develop a therapy that may include generating a pacing signal to be applied to region 210b. The pacing signal delivered by the implantable element 208 induces theta activity in region 210b that may be similar to the theta activity in region 210a. In certain embodiments, at least one of elements 206 and 208 or any additional elements may be used measure other parameters to adjust the pacing signal.

The power supply 234 may include single-charge type energy sources or rechargeable energy sources. Single-charge energy sources are typically disposed after the energy stored within the single-charge energy source is drained. In certain embodiments, single-charge energy sources include disposable alkaline or mercury based batteries. In certain embodiments, the power supply 234 includes rechargeable energy sources. The rechargeable batteries may include one or more Lithium ion batteries. The rechargeable batteries may also include at least one of a lead acid, a nickel metal hydride and a nickel cadmium battery. In other embodiments, the rechargeable energy source includes other soft rechargeable batteries. The rechargeable energy source may also include other capacitive storage type batteries.

Figure 3A:
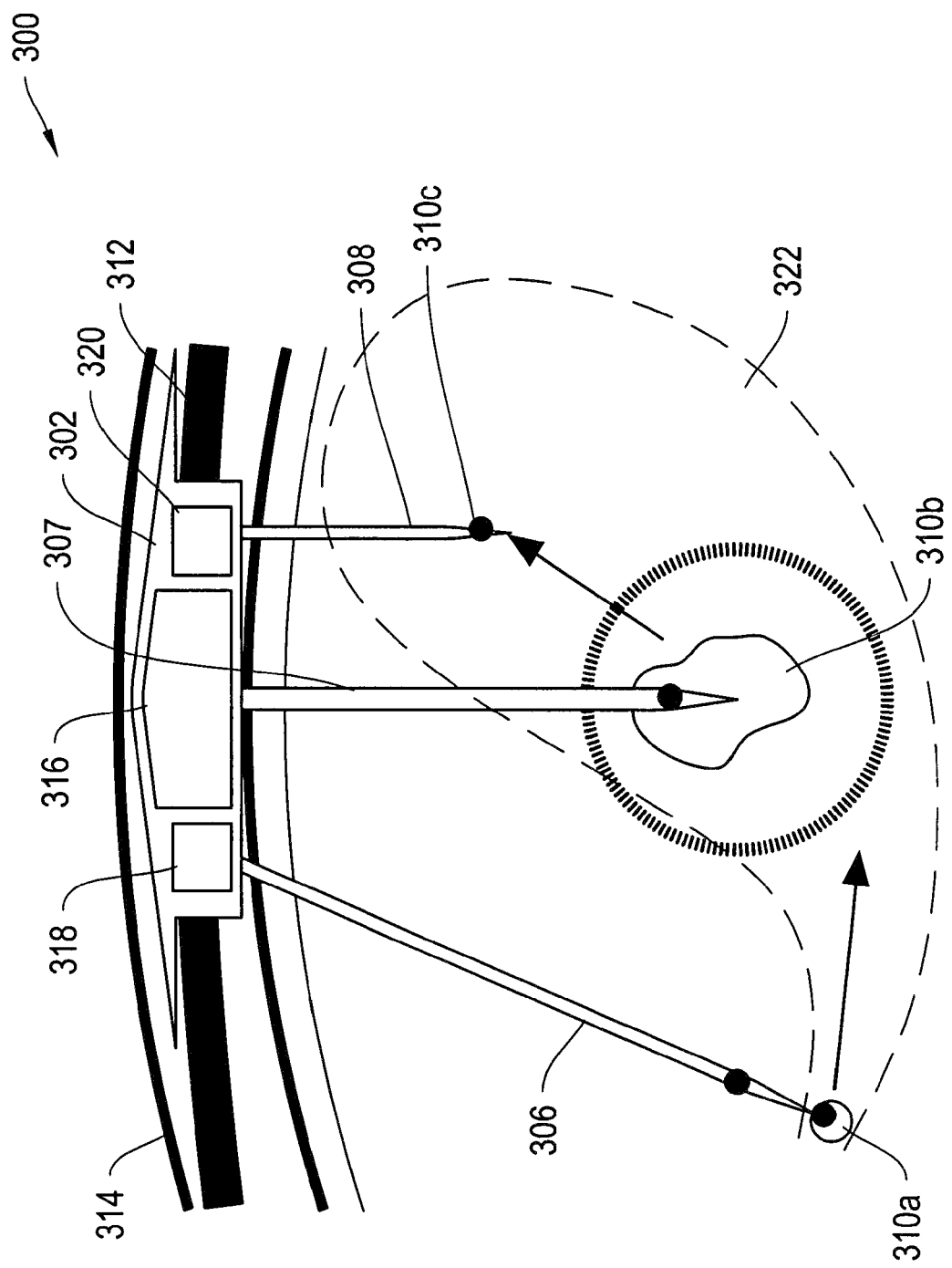

FIG. 3A depicts a therapy system 300 for providing therapy to a neural signaling pathway 322. The neural signaling pathway 322 includes three neural cluster regions 310a, 310b and 310c. The signal pathway may begin at cluster 310a and end at cluster 310c. The three implantable elements 306, 307 and 308 are positioned near each of the three neural clusters 310a, 310b and 310c, respectively. The system includes casing 302 that may be similar to casing 202 for housing the control circuitry. In particular, casing 302 houses control circuitry 316, recording circuitry 318 for recording electrical signals from the neural cluster 310a through implantable element 306, and pacing circuitry 320 for stimulating the neural cluster 310c through implantable element 308.

The implantable element 307 includes a catheter for delivering chemical substances to neural cluster 310b. The control circuitry 316 may also include a chemical reservoir for providing chemical substances to the catheter 307. Implantable element 307 may also include electrical and/or chemical sensors capable of measuring chemical and electrical activity in neural cluster 310b.

During operation, a measurement may be taken by element 306 to determine if the neural pathway 322 is activated. The control circuitry 316 determines if the pathway 322 is activated by measuring the electrical activity in cluster 310a. If the pathway 322 is not yet active, the control circuitry 316 applies a signal (such as a voltage signal) at cluster 310a using implantable element 306. The control circuitry 316 then determines if the pathway 322 is activated at cluster 310b. If the pathway 322 is not active in cluster 310b, the control circuitry delivers a chemical compound to the cluster 310b to induce the neurons to generate an electric field. The element 308 measures the electrical and/or chemical activity in cluster 310c to determine if the signal generated at either regions 310a or 310b has reached region 310c.

Certain types of neurons in the region activate theta rhythms and certain types of neurons in the region inhibit the theta rhythm. In certain embodiments, the implantable elements may be configured to deliver a pacing signal to selectively stimulate each of the activating and inhibiting neurons to induce a desired theta rhythm.

FIG. 3B depicts an exemplary implantable element 324, according to an illustrative embodiment of the invention for inducing a desired theta rhythm by stimulating activating and inhibiting neurons. In particular, element 324 is a directional electrode having one or more conductive channels facing 180 degrees away from another one or more conductive channels. The nucleus pontis oralis and the median raphe nucleues are neuron clusters in the hippocampus that activate and inhibit, respectively, theta activity. The electrode 324 is positioned such that one set of conductive channel faces the nucleus pontis oralis and the other set of conductive channels faces the median raphe nucleus.

In certain embodiments, the electrode 324 may deliver a stimulating or pacing signal to at least one of each of the set of conductive channels. Such an electrode is advantageous because it allows the operations of activation and inhibition to be performed together and avoid conflicts in theta activity generation arising from activating both sets of nuclei or inhibiting both sets of nuclei simultaneously.

As discussed thus far, one or more regions may be stimulated based on measurements made from one or more regions. FIGS. 4A-4C depict various schemes for providing therapy whereby one or more regions (or clusters) are paced.

FIG. 4A is a schematic representation for a scheme to provide therapy to a neural signaling pathway 402. The pathway 402 as shown includes five neural clusters whereby information flows from neural cluster 404a to 404e. It may be desirable to modify the behavior of the pathway 402 to cause a certain behavior associated with a cognitive function. Therefore, there may be a need to record signals from one or more clusters in the pathway 402 and pace one or more selected clusters. In the illustrated embodiment, electrical and/or chemical signals from each of the neural clusters 404a-404e are recorded by the control circuitry 406. The control circuitry 406 may be similar to control circuitry 202 (FIG. 2B). The control circuitry 406 records signals from each of the clusters 404a-404e and determines a suitable therapy including a pacing signal. The pacing signal may be applied to one or more of the clusters. In the illustrated embodiment, the pacing signal is applied to cluster 404c.

The selection of a suitable neural cluster 404c for pacing may depend on convenience to implant, convenience to modify electrical and/or chemical activity in that region, and on resulting side effects. In certain embodiments, during memory formation, certain pathways carrying processing information and certain regions where selective activation occurs may be less suited for pacing and the pacing signal may be applied elsewhere. As an example, during information processing, the Entorhinal Cortex is active, but its activity is processing the data and transporting the data into the hippocampus. There is then a risk that processed information may be lost if the Entorhinal Cortex is paced. As another example, during information processing, the CA3 is selectively activated as the processed information is stored into a selected location. There is then a risk that the storing process may be disrupted if the entire CA3 is paced/stimulated.

In other embodiments, the pacing location may be selected close to the root of the signal pathway. Selecting the pacing location close to the root of the pathway allows for simpler pacing that can activate the entire pathway. However, roots may be located in sensitive regions of the brain such as the brainstem and consequently implantation of electrodes and other implantable elements becomes more difficult. Such a choice of pacing location may result in unwanted stimulation of neighboring clusters not along the pathway. Moreover, in the event that one or more clusters along the pathway are damaged, pacing the cluster near the root of the pathway may not be useful since there might be a break along the pathway near the damaged cluster to hinder the flow of information.

In certain embodiments, the pacing location may be selected at a location of a missing or damaged neural cluster. FIG. 4B depicts such a configuration whereby the control circuitry 406 delivers a pacing signal to cluster 404c. In particular, the control circuitry 406 may record the activity at cluster 404b and generate a pacing signal that, when applied to cluster 404c induces the neurons to generate activity similar to that at cluster 404b. Such a scheme may complete a broken pathway 402.

In other embodiments, the pacing location may be selected close to the end of the signal pathway. In such embodiments, clusters 404d and 404e may be directly paced to bypass damaged cluster 404c based on the activity at cluster 404b. Bypassing the damaged cluster 404c may be necessary if the damage is so extensive that a response cannot be elicited regardless of increased stimulation. Alternatively, as depicted in FIG. 4C, cluster 404c may be functioning, but it might be in close proximity to a cluster 408 that may be a sensitive cluster not along the pathway 402. In such cases, pacing at cluster 404c may influence cluster 408 and thereby cause undesirable side effects. In such cases, the end cluster 404e may be paced based on the activity measured at the first cluster 404a, thereby forming an artificial neural pathway that bypasses the pathway 402.

Figure 5:
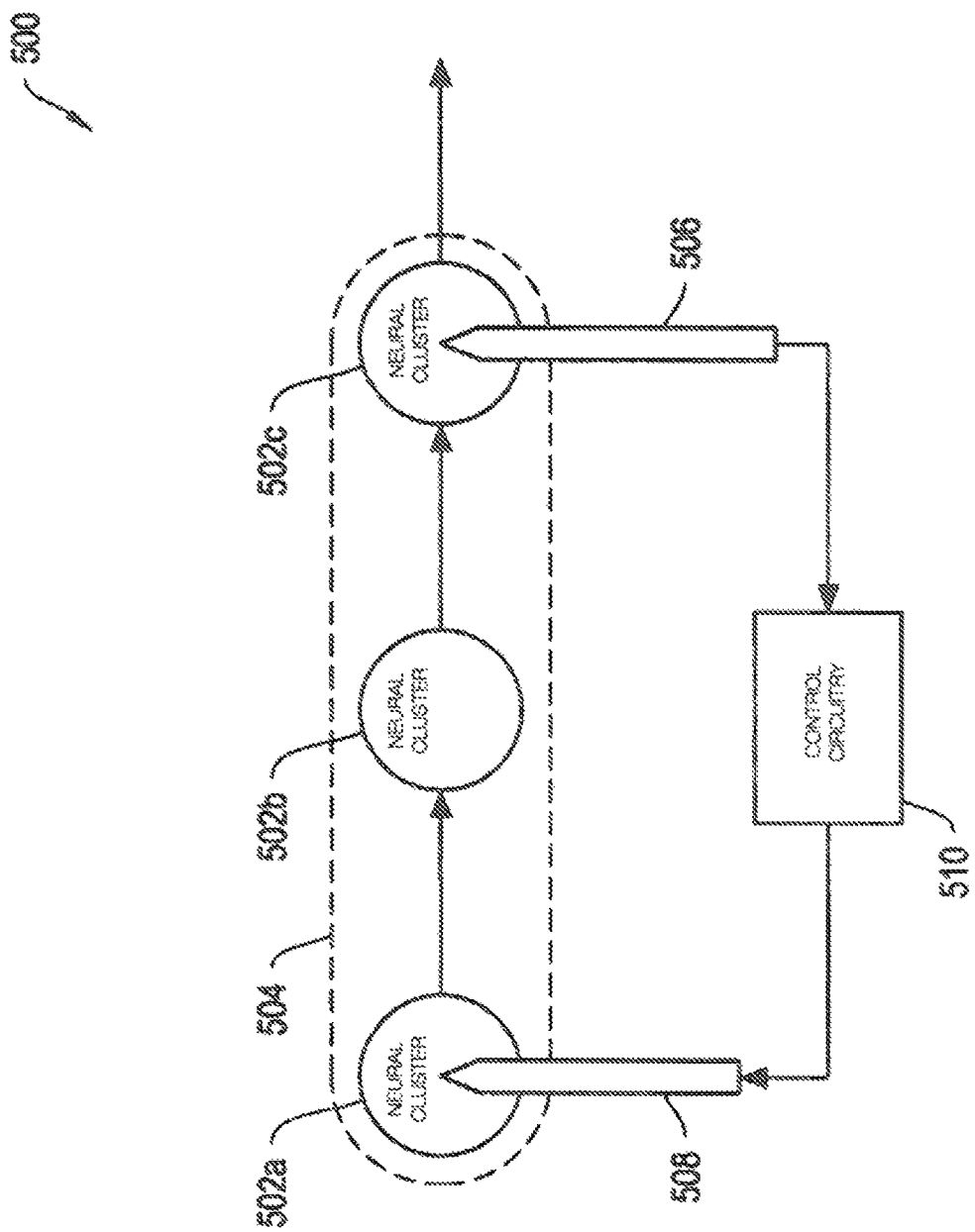
Figure 6:
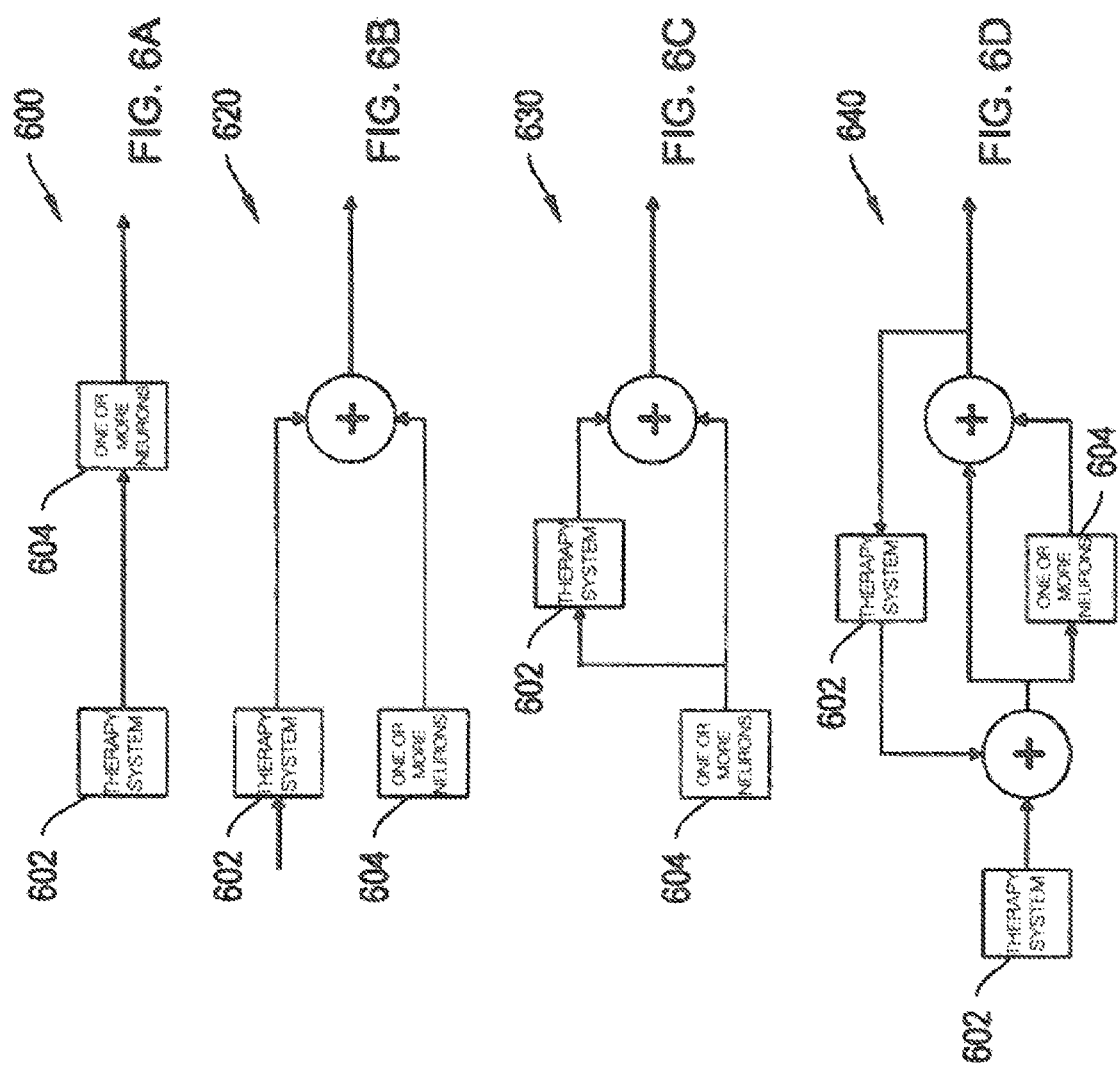
FIGS. 6A-6D depict schemes for combining pacing signals and neural firing patterns of one or more neurons.

FIGS. 5-6D depict various pacing schemes in addition to those depicted in FIGS. 4A-4C that are applied to one or more regions of the brain. In particular, FIG. 5 is a control block diagram depicting a scheme 500 for pacing and providing therapy, according to an illustrative embodiment of the invention. In particular, FIG. 5 depicts a neural signaling pathway including regions or neural clusters 502a, 502b and 502c. Information may flow from node 502a to 502c. Implantable elements 506 and 508 are inserted into regions 502c and 502a, respectively. The implantable elements 506 and 508 are connected to control circuitry 510.

During operation, according to scheme 500, the control circuitry applies a pacing signal in region 502a.

The pacing signal applied at regions 502a is modulated based on a recorded feedback signal measured at region 502c, which may be at the end portion of the pathway 504.

The feedback signals have a smaller amplitude than the pacing signal and provide for a measure of accuracy and effectiveness of the pacing scheme. In particular, pacing effectiveness may be measured by evaluating memory formation to determine if memory is correctly being processed and stored. Electrical activity such as theta rhythm and/or gamma rhythm are quantifiable measures that are used to determine the effectiveness of the pacing scheme. In certain embodiments, chemical concentrations are also suitable measures to determine the effectiveness of a pacing scheme. Behavioral memory assessments, as previously described, may also be used to determine pacing effectiveness. The feedback signal may be any measure that is related to the activity being paced. In certain embodiments, the feedback signal and the activity being paced may follow a one-to-one mapping. The feedback signal may be any signal that changes in response to the application of the pacing signal. In certain embodiments, time latency between a change in the feedback signal in response to a change in the pacing signal is low. The feedback signal may also include any signal that can be measured in a consistent manner from patient to patient and from time to time.

The feedback signal is depicted as being measured from region 502c. However, the feedback signal may be measured in other locations without departing from the scope of the invention. In particular, the feedback signal may be measured in a region having low levels of noise, or substantially constant levels of noise. The feedback signal may be measured in a location that is accessible and can accommodate an implantable element. In certain embodiments, the region has a nucleus from about 2 mm to about 4 mm.

The feedback signal may be measured at a location that the pacing signal can be measured. In certain embodiments, the feedback signal is placed away from a location that is currently being paced.

FIGS. 6A-6D are control block diagrams representing different pacing schemes, some measuring a feedback signal. In particular, FIG. 6A depicts a scheme 600 whereby a therapy system 602 (similar to system 200 of FIGS. 2A and 2B including implantable electrodes and control circuitry) applies a pacing signal to one or more neurons 604 to cause the neuron 604 to alter its firing patterns. As an example, the system 602 may apply a high frequency pulse waveform to a region in the brain to stimulate activating or inhibiting neurons thereby controlling the firing pattern in that region.

FIG. 6B depicts a scheme 620 whereby the pacing signal generated by system 602 is superimposed on a normal firing pattern of one or more neurons 604. In another embodiment, as depicted in scheme 630 in FIG. 6C, the system 602 alters the neuron firing patterns and then superimposes the altered firing pattern on the pacing signal. FIG. 6D depicts a scheme 640 that includes the effect of a feedback measurement made by the system 602.

In certain embodiments, in addition to measuring pacing effectiveness and providing real-time feedback to the therapy system, one or more signals may be recorded in the brain to determine a suitable type or mode of therapy. For example, as noted earlier, memory formation occurs in two steps—information processing and information consolidation. During each of these steps, neuronal activity tends to be different and consequently the brain may require different types of therapy. One or more signals from the brain may be used to determine whether it is currently processing information or consolidating information. As an example, if the brain is currently processing information, the therapy system may induce a hippocampal theta rhythm and if the brain is currently consolidating information, the therapy system may switch modes and induce sharp waves.

Information processing naturally tends to occur during wake hours and/or other alert times, especially when a patient is concentrating. Information consolidation naturally tends to occur during sleep hours and/or other inactive times including when the patient is awake but doing routine tasks. When a patient is alert, theta oscillations and sodium spike activity are involved in the continuous recording of activity in the hippocampus. The amount of neurotransmitters in the hippocampus decreases, however, during slow wave sleep, awake immobility, drinking, eating, face washing, and grooming. Decreased release of neurotransmitters in turn inhibits the steady potassium current necessary to maintain sustained sodium spike activity. This results in the conversion of hippocampal and cortical cells to a bursting firing mode, characterized by the appearance of sharp waves. Increased calcium is released as a result of the burst in firing, which is hypothesized to play a role in memory consolidation. It then follows that methods for specifically improving information processing should be performed when a patient is highly alert, while methods for specifically improving information consolidation should be performed when a patient is not highly alert, specifically when the hippocampal cells are in bursting firing mode.

According to the present application, different alertness levels of a patient may be determined. Alertness levels can be inferred from other brain activities that have been commonly analyzed via electroencephalography or EEG signals. For example, as a person falls asleep or looses concentration, brain activity is modulated, representing different depths and phases of consciousness and attentiveness. A typical persons transitions through different levels of brain activity over time, starting at a first sleep state known as slow wave sleep or SWS. SWS has low frequency high power EEG activity. The sleep may lighten into so-called intermediate sleep states. Another sleep state known as rapid eye movement sleep is characterized by a lower power EEG activity. An alertness level may be described as any distinguishable sleep or wakefulness that is representative of behavioral, physical or signal characteristics. Awake states may actually be part of the sleep state, i.e., part of a low alertness level, and the awake states can be characterized by vigilance into attentiveness or levels of alertness.

The alertness level of a patient can be measured from at least one of alpha, beta and theta activity in the brain. The alertness level may also be set by a patient or another user based on whether or not the patient is alert in one or more of their senses including sight, hearing, smell, touch and taste.

In certain embodiments, the therapy system has at least two operating modes for two steps in memory formation and these modes correspond to the alertness level of the patient. In some embodiments, a high alertness level is characterized by hippocampal and/or cortical theta rhythm, while a low alertness level is characterized by the lack of hippocampal and/or cortical theta rhythm.

Figure 7:
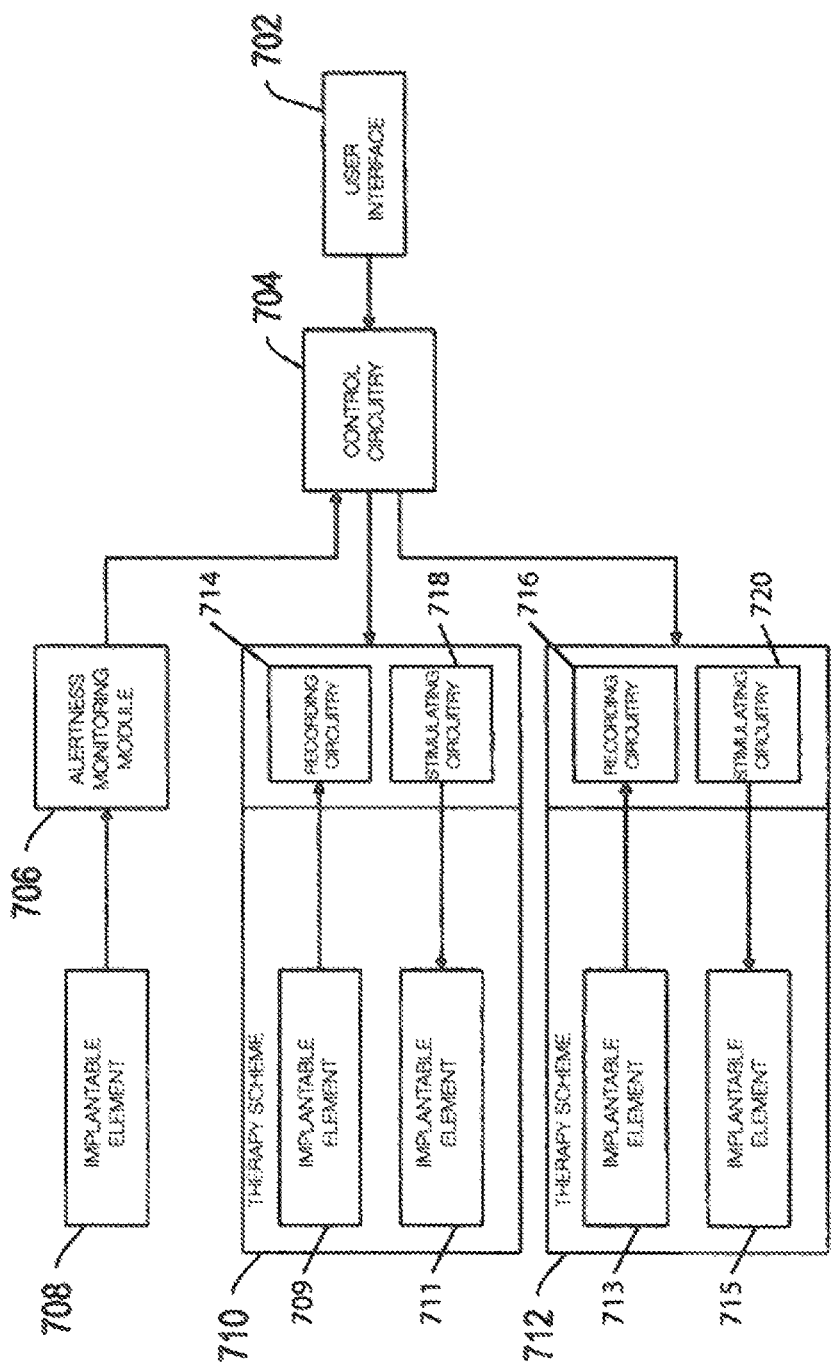
FIG. 7 depicts an illustrative mode-based scheme for delivering therapy.

FIG. 7 is a block diagram depicting a mode-based therapy system 700. The system 700 includes a user interface 702 capable of receiving an alertness level from a user and an alertness monitoring module 706 including an implantable element 708 and control circuitry for measuring the alertness of the patient. The system 700 further includes control circuitry 704 that is configured to determine a mode of therapy based on the alertness level determined by the alertness monitoring module 706 and the user configured alertness level from the user interface 702. The user interface 702 may include an option to either manually or automatically determine the alertness of the patient.

The control circuitry 704, after determining the mode of therapy, applies the corresponding therapy scheme 710 or 712 (e.g., pacing signal) to a region of the brain. In the illustrated embodiment, each a the therapy schemes 710 and 712 include two implantable elements 709, 711, 713, and 715 for recording 714 and 716 stimulating 718 and 720 electrical and/or chemical activity in the brain.

In certain embodiments the therapy scheme 710 is applied during the information processing stage of memory formation and includes the measurement of neuronal activities typically relevant to information processing including theta rhythm, gamma activity and sodium concentration. The therapy scheme 712 may be applied during the information consolidation stage of memory formation and includes the measurement of neuronal activities such as bursting activity and calcium concentrations.

As noted earlier, the therapy systems include implantable elements such as electrodes and chemical sensors for measuring activity and applying signals to one or more regions in the brain. These therapy systems also include control circuitry configured to automatically provide therapy for extended periods of time. However, typical implantable elements, used to measure electrical and chemical activity in the brain, tend to fail or migrate after a certain period of time. This may be due, at least in part, to the fact that these implantable elements such as electrodes used to record single neuron activity typically have a high impedance and a small contact surface.

FIGS. 8A-8D depict typical problems encountered when recording neuronal signals. FIG. 8A depicts an electrode 800 having a recording contact 802 and a conductive track 803. The electrode 800 may be configured to record neuronal activity occurring within a volume 804 around the contact 802. The electrode may be capable of recording electrical activity from a neuron 805 within the volume 804.

However, in time, as depicted in FIG. 8B, Glial scarring tissue 808 covers the contact surface 802, thereby preventing the conductors in the electrode from interfacing with the extracellular fluid. As a result, the electrode may no longer be able to measure activity from the neuron 805.

As shown in FIG. 8C, the contact surface 802 of the electrode may also suffer from erosion thereby decreasing the recording volume 804. As a result, the neuron 805 may fall outside of the eroded recording volume 804 and the electrode may no longer be able to record activity from the neuron 805.

The electrode may migrate and, as depicted in FIG. 8D, even small migrations can cause the neuron 805 to fall outside of the volume 804. As a result, the electrode may no longer be able to record activity from neuron 805.

In certain embodiments, the electrodes used to measure local field potential, which may be a summation of activities from multiple neurons in close proximity, have larger contact surfaces than the electrodes used to measure single neuron activity. These electrodes (long-term electrode) tend to last longer than the electrodes (short-term electrodes) used to measure single neuron activity.

FIGS. 9A and 9B depict a system method for combining the specificity of a short term electrode with the longevity and spatial independence of a long term electrode. In particular, FIG. 9A depicts a system 900 having an electrode 902 for recording single neuron activity (short term electrode) and an electrode 904 for recording local field potential (long term electrode).

The electrodes 902 and 904 are connected to an implantable pulse generator (IPG) 906 that includes a processor 908 and a pulse generator 910. The IPG 906 may be similar to the control circuitry 202 of FIG. 2. The pulse generator 910 delivers a pacing signals to the stimulation electrodes 912. The stimulation electrodes 912 provide natural activity information at the stimulation site to the processor 908.

In certain embodiments, the electrodes 902 are implanted in a location where theta activity is generated, such as the hippocampus. The electrode 904 may be implanted in a location where a component of the local field potential is the theta activity information. The stimulation electrode 912 may be implanted in a location where theta activity can be elicited, such as the fornix or the septal region. The IPG 906 may be implanted in the body close to the electrodes.

During operation, the system 900 initially uses the measurements from electrodes 902 and 904 to train an inference engine. The inference engine may correlate the long term signal to the short term signal. In the event that the short term electrode 902 fails, the system 900, with the aid of the inference engine in the processor 908, infers a feedback signal from the signal obtained from long-term electrode 904. This feedback signal helps the processor 908 to determine an appropriate pacing signal.

As depicted in FIGS. 9B-9D, the system 900 may operate in three modes including a training mode (FIG. 9B), a learning mode (FIG. 9C) and a regular mode (FIG. 9D). During training mode, the processor 908 receives input signals from short-term electrode 902 and long-term electrode 904 and uses each of the inputs to train an inference engine.

In certain embodiments, more than one long-term electrode is used. The inference engine may include circuitry configured to run an artificial intelligent scheme that teaches itself to interpret long-term data. For instance, the circuitry may include an artificial neural network or HMM. In certain embodiments, the scheme includes a signal source localization scheme. The inference engine may further include circuitry for measuring the life of a short term electrode. In certain embodiments, the inference engine may include circuitry for measuring impedance and/or signal-to-noise ratio of the electrode. The inference engine may have a module that regularly checks whether the short term electrode is still working. The module may be configured to check the impedance level and once the impedance crosses a certain threshold, the short term electrode may be deemed to have failed and the inference engine switches from training to functioning.

The processor 908 generates a pacing signal based on the input signals from the short-term electrode 902 and from an archive of one or more memory exercises performed by the patient. During the learning mode (FIG. 9C), the patient performs a series of memory exercises under supervision. During this mode, the stimulation electrode 912 continues to record data that it sends back to the processor 908. The supervising attendant may keep a log of the positive memory trials such that the corresponding positive activity at the stimulation site can be re-generated at a later time by the processor 908. The results of the positive memory trials along with the corresponding positive activity at the stimulation site can be archived and saved either within the IPG (906) or in an external storage device.

As depicted in FIG. 9D, during the regular mode, the long term electrode 904 records signals which are received by the inference engine in the processor 908. The inference engine infers a pacing signal based on the input signal from the long term electrode.

In certain embodiments, the system 900 is configured to detect when a patient is making or about to make a negative memory recall. The system 900 includes circuitry capable of detecting inputs received from the electrodes and/or from external stimuli and determining based on at least the nature of the inputs, whether the patient is making or about to make a negative recall. In certain embodiments, external input in the form of patient or care-giver suggestion, the system may determine that the patient is making or about to make a negative memory recall. In response to determining that the patient is making or about to make a negative memory recall, the system 900 may deliver a pacing signal to induce the neurons in the brain to generate activity that corresponds to a positive memory recall.

In certain embodiments, the system 900 monitors inputs received from one or more electrodes and calculates statistics (such as averages) of the electrical and/or chemical activity of at least a portion of the brain. Based on the calculated statistics (i.e., if the calculated statistic crosses a threshold value), the system 900 may predict whether the patient is about to make a positive or negative memory recall and administer therapy accordingly.

Figure 10:
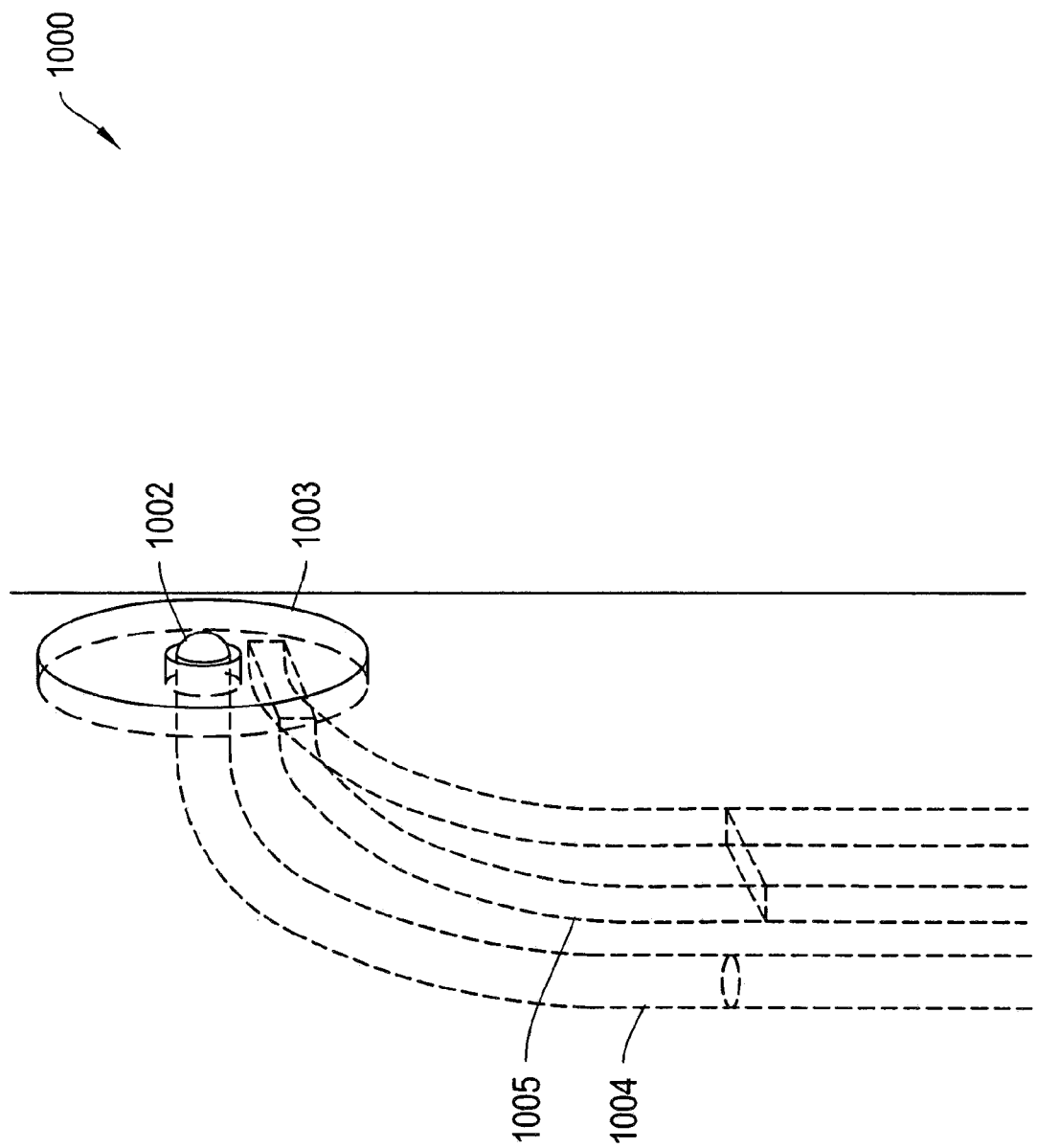
FIG. 10 depicts recording electrodes, according to an illustrative embodiment of the invention.

FIG. 10 depicts an implantable electrode 1000 having a long term electrode component and a short term electrode component. In particular, the short term component includes small conductive contact 1002 and the long term component includes a large conductive contact 1003 that is concentric with the small contact 1002. Each contact 1002 and 1003 has separate conductive tracks 1004 and 1005, respectively. The short term electrode component is capable of recording electrical activity within the volume 1009 and including neuron 1012. The long term electrode component is capable of recording electrical activity within a larger volume 1007 that includes neurons 1012 and 1014.

As noted above, the order in which the steps of the present method are performed is purely illustrative in nature. In fact, the steps can be performed in any order or in parallel, unless otherwise indicated by the present disclosure. The invention may be embodied in other specific forms without departing from the spirit or essential characteristics thereof. The forgoing embodiments are each therefore to be considered in all respects illustrative, rather than limiting of the invention.

What is claimed is:

1. A method of improving a cognitive function in a patient, comprising: (a) receiving a set of inputs from a first region in a patients brain, (b) correlating the set of inputs with a set of neurophysiological markers of a cognitive function, and (c) improving the cognitive function in the patients brain by inducing a response in a second region of the brain, which response is selected based upon the correlations of step (b), wherein the first region in the brain exhibits activity indicative of memory readiness.

2. The method of claim 1, wherein the cognitive function includes memory.

3. The method of claim 1, further comprising determining an alertness level.

4. The method of claim 3, wherein the response is selected further based upon the alertness level.

5. The method of claim 3, wherein a location of the second region is based on the alertness level.

6. The method of claim 3, wherein the alertness level is based on a state of consciousness of the patient including at least one of awake, alert, sleep and unconsciousness.

7. The method of claim 3, wherein the alertness level is based on whether the patients brain is performing at least one of information processing, information consolidation and information recall.

8. The method of claim 3, wherein the alertness level is determined by a user.

9. The method of claim 3, wherein the alertness level is determined based on the set of inputs.

10. The method of claim 9, wherein the set of inputs includes at least one of theta activity, delta activity, and alpha activity, recorded from hippocampus and neocortex, and rhythmic discharges from supramammillary nucleus and medial septum.

11. The method of claim 9, wherein the patient exhibits at least two alertness levels.

12. The method of claim 11, wherein improving the cognitive function comprises inducing at least two different responses that correspond to the at least two alertness levels.

13. The method of claim 12, wherein improving the cognitive function comprises inducing neurons in the second region of the brain to generate hippocampal theta rhythm when alertness level is set high, and inducing neurons in the second region of the brain to generate hippocampal sharp waves when alertness level is set low.

14. The method of claim 1, wherein receiving a set of inputs includes measuring at least one of an electrical signal and a chemical signal.

15. The method of claim 14, wherein the first region includes at least one of hippocampus and neocortex.

16. The method of claim 14, wherein the set of neurophysiological markers includes at least one of hippocampal theta and cortical theta activity.

17. The method of claim 1, wherein inducing a response includes delivering at least one of an electrical signal and a chemical signal to neurons in the second region in the brain.

18. The method of claim 17, wherein the cognitive function is improved by inducing at least one of a hippocampal theta rhythm, hippocampal sharp waves and gamma activity.

19. The method of claim 18, wherein the theta rhythm is induced by stimulating at least one of activating neurons and inhibiting neurons in the second region.

20. The method of claim 18, wherein the hippocampal sharp waves are induced by stimulating at least one of activating neurons and inhibiting neurons in the second region.

21. The method of claim 1, wherein the second region includes at least one of hippocampus, medial septum, fornix, fimbria, supramammillary nucleus, posterior hypothalamus, nucleus basalis Meynert, nucleus pontis oralis and median raphe nucleus.

22. The method of claim 18, wherein the gamma activities are induced by stimulating at least one of activating neurons and inhibiting neurons in the second region.

23. The method of claim 1, wherein inducing a response includes inducing neurons in the second region of the patients brain to generate a signal that is substantially similar to the at least one of the set of inputs.

24. The method of claim 1, wherein the cognitive function includes positive memory events.

25. The method of claim 24, further comprising predicting negative memory events based on the inputs from the first region, and applying a signal that is substantially similar to the activity observed at the second region during positive memory events.

26. The method of claim 24, further comprising building a database of positive memory events and negative memory events based on a set of cognitive exercises performed by the patient.

27. The method of claim 1, wherein at least one of the first region and the second region comprises a neural signaling pathway that includes neurons connecting at least two of CA1, CA2, CA3, Dentate Gyrus, Entorhinal Cortex, Hilus, and subiculum.

28. The method of claim 1, wherein at least one of the first region and the second region comprises a neural signaling pathway that includes neurons connecting at least two of posterior nucleus hypothalamus, supramammillary nucleus, medial septum, hippocampus, neocortex.

29. The method of claim 1, wherein at least one of the first region and the second region comprises a neural signaling pathway that includes the Perforant Path, Schaffer Collateral Pathway, and Associational Commissural Pathway.

30. A system for improving a cognitive function, comprising: a plurality of implantable elements for sensing and delivering signals within a brain; control circuitry configured to: receive a set of inputs from at least one of the plurality of implantable elements, correlate the set of inputs with a set of neurophysiological markers of a cognitive function, determine a response based on said correlations, and induce the response in the brain using at least one of the plurality of implantable elements; and at least one training mode and at least one functioning mode.

31. The system of claim 30, wherein the implantable elements include electrodes capable of recording and generating electrical signals.

32. The system of claim 30, wherein the implantable elements include sensors capable of sensing chemical concentration.

33. The system of claim 30, wherein the implantable elements include catheters for delivering chemicals to the brain.

34. The system of claim 33, wherein the implantable elements include a reservoir for supplying chemicals to the brain.

35. The system of claim 30, wherein the implantable elements include at least one short term electrode, and at least one long term electrode, and the control circuitry is further configured to determine if the short term electrode is functioning, in response to determining that the short term electrode is functioning, receive a first set of inputs from the at least one short term electrode and a second set of inputs from the at least one long term electrode, and associate one or more of the first set of inputs with one or more of the second set of inputs in response to determining that the short term electrode has failed, infer a first set of inputs based on the second set of inputs.

36. The system of claim 30, further comprising a database of activities observed in the brain during positive memory events.

37. The system of claim 36, wherein the control circuitry is further configured to: populate the database of activities during the training mode, and apply the activities in the database to the brain during the functioning mode.

38. The system of claim 36, further comprising a database of activity observed in the brain during negative memory events.

39. The system of claim 38, wherein the control circuitry is further configured to: populate both databases during the training mode, and identify negative memory events based on referencing the inputs from the first region to the database of negative memory events and apply the corresponding activity from the database of positive memory events during function mode.

40. A method of improving a cognitive function in a patient, comprising: (a) receiving a set of inputs from a first region in the patient's brain, (b) correlating the set of inputs with a set of neurophysiological markers of a cognitive function, (c) determining an alertness level of the patient based on the set of inputs, and (d) improving the cognitive function in the patients brain by inducing a response in a second region of the brain, which response is selected based upon the correlations of step (b), wherein when the patient exhibits at least two alertness levels, improving the cognitive function comprises inducing at least two different responses that correspond to the at least two alertness levels, and wherein inducing at least two different responses comprises inducing neurons in the second region of the brain to generate hippocampal theta rhythm when alertness level is set high, and inducing neurons in the second region of the brain to generate hippocampal sharp waves when alertness level is set low.

41. A method of improving a cognitive function in a patient, comprising: (a) receiving, a set of inputs from a first region in a patient's brain, (b) correlating the set of inputs with a set of neurophysiological markers of a cognitive function, and (c) improving the cognitive function in the patients brain by inducing a response in a second region of the brain by delivering at least one of an electrical signal and a chemical signal to neurons in the second region in the brain, which response is selected based upon the correlations of step (b), wherein the cognitive function is improved by inducing at least one of a hippocampal theta rhythm, hippocampal sharp waves and gamma activity, and wherein the theta rhythm is induced by stimulating at least one of activating neurons and inhibiting neurons in the second region.

42. A method of improving a cognitive function in a patient, comprising: (a) receiving a set of inputs from a first region in a patient's brain, (b) correlating the set of inputs with a set of neurophysiological markers of a cognitive function, and (c) improving the cognitive function in the patients brain by inducing a response in a second region of the brain by delivering at least one of an electrical signal and a chemical signal to neurons in the second region in the brain, which response is selected based upon the correlations of step (b), wherein the cognitive function is improved by inducing at least one of a hippocampal theta rhythm, hippocampal sharp waves and gamma activity, and wherein the hippocampal sharp waves are induced by stimulating at least one of activating neurons and inhibiting neurons in the second region.

43. A method of improving a cognitive function in a patient, comprising: (a) receiving a set of inputs from a first region in a patient's brain, (b) correlating the set of inputs with a set of neurophysiological markers of a cognitive function, and (c) improving the cognitive function in the patients brain by inducing a response in a second region of the brain by delivering at least one of an electrical signal and a chemical signal to neurons in the second region in the brain, which response is selected based upon the correlations of step (b), wherein the cognitive function is improved by inducing at least one of a hippocampal theta rhythm, hippocampal sharp waves and gamma activity, and wherein the gamma activities are induced by stimulating at least one of activating neurons and inhibiting neurons in the second region.

44. A system for improving a cognitive function, comprising: a plurality of implantable elements for sensing and delivering signals within a first region of a brain; and control circuitry configured to: receive a set of inputs from at least one of the plurality of implantable elements, correlate the set of inputs with a set of neurophysiological markers of a cognitive function, determine a response based on said correlations, and induce the response in a second region of the brain using at least one of the plurality of implantable elements, wherein the implantable elements include at least one short term electrode, and at least one long term electrode, and the control circuitry is further configured to: determine if the short term electrode is functioning, in response to determining that the short term electrode is functioning, receive a first set of inputs from the at least one short term electrode and second set of inputs from the at least one long term electrode, and associate one or more of the first set of inputs with one or more of the second set of inputs in response to determining that the short term electrode has failed, infer a first set of inputs based on the second set of inputs.

* * * * *